(12) United States Patent
Ogawa

(10) Patent No.: US 12,059,229 B2
(45) Date of Patent: Aug. 13, 2024

(54) NURSE CALL SYSTEM

(71) Applicant: Aiphone Co., Ltd., Nagoya (JP)

(72) Inventor: Kenichi Ogawa, Nagoya (JP)

(73) Assignee: Aiphone Co., Ltd., Nagoya (JP)

( * ) Notice: Subject to any disclaimer, the term of this patent is extended or adjusted under 35 U.S.C. 154(b) by 1071 days.

(21) Appl. No.: 16/923,467

(22) Filed: Jul. 8, 2020

(65) Prior Publication Data

US 2020/0342983 A1  Oct. 29, 2020

Related U.S. Application Data

(63) Continuation of application No. PCT/JP2018/015902, filed on Apr. 17, 2018.

(30) Foreign Application Priority Data

Jan. 16, 2018 (JP) .................................. 2018-005122
Feb. 2, 2018 (JP) .................................. 2018-017514
(Continued)

(51) Int. Cl.
*A61B 5/00* (2006.01)
*G10L 15/08* (2006.01)
(Continued)

(52) U.S. Cl.
CPC .......... *A61B 5/0002* (2013.01); *A61B 5/0015* (2013.01); *A61B 5/002* (2013.01);
(Continued)

(58) Field of Classification Search
CPC ......... A61B 5/00; A61B 5/002; A61B 5/1115; A61G 7/05; A61G 7/0506; A61G 7/0524;
(Continued)

(56) References Cited

U.S. PATENT DOCUMENTS 2,740,842 A * 4/1956 Schneider .............. G08B 5/221
379/376.01
5,561,412 A * 10/1996 Novak ................. G08B 25/014
340/286.07
(Continued)

FOREIGN PATENT DOCUMENTS

JP    2001-325363 A1    11/2001
JP    2002-009957 A      1/2002
(Continued)

OTHER PUBLICATIONS

NPL Search (Sep. 21, 2023).*
International Search Report and Written Opinion (Application No. PCT/JP2018/015902) dated Jun. 12, 2018.
Japanese Office Action (Application No. 2018-005122) dated Aug. 3, 2021 (with English translation).

*Primary Examiner* — Van T Trieu
(74) *Attorney, Agent, or Firm* — BURR PATENT LAW, PLLC

(57) ABSTRACT

A nurse call system includes a nurse call slave device, a nurse call master device, a plate slave device, a bedside monitor, a corridor light, a control unit, and nurse mobile phones. The nurse call slave device is provided for each bed in a hospital room for allowing a hospitalized patient to call a nurse. The nurse call master device is provided at a nurse station for answering a call from the nurse call slave device. The plate slave device, the corridor light, or the control unit has an automatic answering unit for automatically answering a call from the nurse call slave device, and causes the automatic answering unit to automatically answer at least a part of calls from the nurse call slave device without calling the nurse call master device and the nurse mobile phones.

6 Claims, 25 Drawing Sheets

(30) Foreign Application Priority Data

Feb. 23, 2018 (JP) .................................. 2018-031147
Feb. 28, 2018 (JP) .................................. 2018-034650
Mar. 19, 2018 (JP) .................................. 2018-051337

(51) Int. Cl.
  *G16H 40/20* (2018.01)
  *G16H 40/63* (2018.01)
  *H04W 4/029* (2018.01)
  *H04W 84/20* (2009.01)

(52) U.S. Cl.
  CPC ........ *G10L 15/08* (2013.01); *G10L 2015/088* (2013.01); *G16H 40/20* (2018.01); *G16H 40/63* (2018.01); *H04W 4/029* (2018.02); *H04W 84/20* (2013.01)

(58) Field of Classification Search
  CPC ... H04B 7/15; H04B 5/00; H04B 5/02; G08B 1/08; G08B 21/02; G08B 21/028; G08B 23/00
  See application file for complete search history.

(56) References Cited

U.S. PATENT DOCUMENTS

| | | | | |
|---|---|---|---|---|
| 2006/0049936 | A1* | 3/2006 | Collins | G08B 21/028 |
| | | | | 340/539.11 |
| 2019/0183705 | A1* | 6/2019 | Bodurka | A61G 7/05 |
| 2020/0342983 | A1* | 10/2020 | Ogawa | G16H 40/63 |

FOREIGN PATENT DOCUMENTS

| | | |
|---|---|---|
| JP | 2003-259018 A1 | 9/2003 |
| JP | 2005-210173 A1 | 8/2005 |
| JP | 2006-145376 A | 6/2006 |
| JP | 2006-255007 A1 | 9/2006 |
| JP | 2009-207548 A1 | 9/2009 |
| JP | 2014-042711 A1 | 3/2014 |
| JP | 2014-087524 A1 | 5/2014 |
| JP | 2014-097116 A1 | 5/2014 |
| JP | 2015-058262 A1 | 3/2015 |
| JP | 2015-130622 A1 | 7/2015 |
| JP | 2016-087356 A1 | 5/2016 |
| JP | 2017-144024 A1 | 8/2017 |
| WO | 2017/003847 A1 | 3/2017 |

* cited by examiner

NURSE CALL SYSTEM

This application is a Continuation of International Application No. PCT/JP2018/015902 filed on Apr. 17, 2018, which claims the benefit of the Japanese Patent Application No. 2018-005122 filed on Jan. 16, 2018, No. 2018-017514 filed on Feb. 2, 2018, No. 2018-031147 filed on Feb. 23, 2018, No. 2018-034650 filed on Feb. 28, 2018, and No. 2018-051337 filed on Mar. 19, 2018, the disclosures of which are incorporated by reference herein in their entireties.

BACKGROUND OF THE INVENTION

Field of the Invention

The present invention relates to a nurse call system.

Description of Related Art

Conventionally, a nurse call system in which, when a call is made using a nurse call slave device provided to an individual bed, a nurse call master device provided at a nurse station, or the like is notified of the call, has been widespread. In such a nurse call system, a bed number and a name of a patient who has made the call is displayed on a display unit in the called nurse call master device or the like, and a nurse is allowed to recognize the patient who made the call through the display, and answer the call.

Meanwhile, a nurse, who is carrying a nurse mobile phone capable of answering a call from the nurse call slave device, regularly performs nursing rounds throughout hospital rooms of hospitalized patients to whom the nurse is assigned.

The related art is disclosed in Japanese Laid-Open Patent Publication No. 2014-042711 (Patent Document 1), Japanese Laid-Open Patent Publication No. 2005-210173 (Patent Document 2), Japanese Laid-Open Patent Publication No. 2014-087524 (Patent Document 3), and Japanese Laid-Open Patent Publication No. 2014-97116 (Patent Document 4).

However, the nurse does not perform nursing rounds at the exact fixed time every day. Therefore, the hospitalized patients cannot know when the nurse performs nursing rounds, and the hospitalized patient may be absent when the nurse visits the hospital room in the nursing rounds. When the hospitalized patient is absent, the nurse needs to visit the hospital room of the hospitalized patient later again for the nursing rounds, thereby increasing load of the nursing work.

Contents in the calls from the nurse call slave device of the hospitalized patient are various, and may include a content that requires highly urgent handling, a content that does not require highly urgent handling, a content that requires handling by the assigned nurse, a content that requires handling by any nurse, and a wrong call. The nurse needs to answer each call from the nurse call slave device regardless of the content, thereby increasing load of the nursing work.

In the nursing rounds that are regularly performed by a nurse, the nurse needs to measure vital signs such as pulses and body temperatures of the hospitalized patients in addition to performing interviews about their physical conditions and the like. When the hospitalized patient is absent, the nurse needs to visit the hospital room again, so that it takes a long time to complete the nursing rounds, thereby increasing load of the nursing work.

In a case where a nurse is assigned to many hospitalized patients, a very long time is required for completing the nursing rounds, and the nursing rounds to be performed several times a day increase a load of their nursing work.

In such a nurse call system, both a nurse call slave device and a bedside monitor are disposed for each bed to provide a patient with various information for enhancing the services for the hospitalized patient, as disclosed in, for example, Patent Document 4. Furthermore, according to Patent Document 4, treatment records of the patients can be inputted from the bedside monitors, and a load of inputting the nursing records to a dedicated terminal after the nurses return to the nurse station is reduced. In the nurse call system disclosed in Patent Document 4, although the treatment records can be inputted in the hospital rooms in which the patients are treated, to reduce load and time for making inputs after the nurses return to the nurse station, many nursing records need to be inputted through the dedicated terminal in the nurse station. Therefore, the load cannot be substantially reduced.

The present invention has been made in view of the aforementioned circumstances, and an object of the present invention is to provide a nurse call system that reduces load of nursing work on nurses, more specifically, a nurse call system that can notify a hospitalized patient that her/his assigned nurse has started nursing rounds, a nurse call system that does not immediately call a nurse call master device or the like for at least a part of calls from nurse call slave devices, a nurse call system that allows hospitalized patients to measure vital signs by themselves, a nurse call system that allows nurses to confirm the state of hospitalized patients without visiting the hospital rooms, and a nurse call system that facilitates input of nursing records.

SUMMARY OF THE INVENTION

In response to the above issues, the inventor of the present invention suggests a nurse call system as described below.

A nurse call system according to a first aspect of the present invention includes a nurse call slave device, a nurse call master device, a plate slave device, a bedside monitor, a control unit, a plurality of nurse mobile phones, and a plurality of hospitalized patient mobile phones. The nurse call slave device is provided for each bed in a hospital room for allowing a hospitalized patient to call a nurse. The nurse call master device is provided at a nurse station for answering a call from the nurse call slave device. The plate slave device, to which the nurse call slave device is connected, is provided near a bed in the hospital room. The bedside monitor is provided for each bed in the hospital room and is capable of displaying patient-related information. The control unit is configured to control calling and speaking, and communication between devices. The plurality of nurse mobile phones are carried by nurses for answering a call from the nurse call slave device. The plurality of nurse mobile phones are connected to the control unit via a PBX having a mobile phone exchange connection function and a base station having a mobile phone wireless transmission/reception function. The plurality of hospitalized patient mobile phones are carried by hospitalized patients. In the nurse call system, a location information transmitter for wirelessly transmitting a location signal is disposed at an appropriate place in a hospital ward, and a location management server for storing location information of each of the nurse mobile phones is provided. Each nurse mobile phone includes a location information communication unit for receiving the location signal transmitted by the location information transmitter, and transmitting the location signal with an ID of the nurse mobile phone added thereto. The location management server includes a nurse mobile phone location storage unit, a nurse mobile phone table storage unit, an assigned nurse table storage unit, a hospitalized patient table storage unit, a bed location storage unit, and a distance measurement unit. The nurse mobile phone location storage unit stores the location information received from each nurse mobile phone. In the nurse mobile phone table storage unit, a nurse and each nurse mobile phone are associated with each other. In the assigned nurse table storage unit, a nurse and a hospitalized patient are associated with each other. In the hospitalized patient table storage unit, a hospitalized patient and the nurse call slave device are associated with each other. The bed location storage unit stores a location of the individual nurse call slave device. The distance measurement unit measures a distance between each nurse mobile phone and the nurse call slave device, and sequentially selects hospitalized patients who satisfy a predetermined condition including the distance. Each nurse mobile phone has a nursing-rounds start button. When a nursing-rounds start operation is performed from any of the nurse mobile phones, the control unit causes the location management server to sequentially select hospitalized patients who satisfy the predetermined condition based on the location information of the nurse mobile phone. Then, the control unit performs control to transmit a nursing-rounds start signal to at least one device among the bedside monitor, the nurse call slave device, the plate slave device, and the hospitalized patient mobile phone of each of the hospitalized patients selected by the location management server. The device that has received the nursing-rounds start signal is controlled to make notification that nursing rounds have started.

In the nurse call system having such a configuration, in a case where the nursing-rounds start operation is performed from the nurse mobile phone, the nursing-rounds start signal is transmitted to at least one device among the bedside monitor, the nurse call slave device, the plate slave device, and the hospitalized patient mobile phone of a hospitalized patient selected by the location management server. The device that has received the nursing-rounds start signal is controlled to make notification that the nursing rounds have started. Therefore, the hospitalized patient can be notified that the nursing rounds by an assigned nurse have started. Thus, the hospitalized patient can prepare for the nursing rounds without freely leaving the hospital room, and, when the nurse visits the hospital room for the nursing rounds, the hospitalized patient is less likely to be absent, thereby enhancing efficiency of the nursing work.

Furthermore, the hospitalized patient is notified in advance that the nursing rounds start, and the nurse does not suddenly visit the hospitalized patient for the nursing rounds, thereby enhancing the privacy of the hospitalized patient.

The distance measurement unit of the location management server may sequentially select hospitalized patients who satisfy the predetermined condition including the distance.

For example, the distance measurement unit may select hospitalized patients associated with the nurse mobile phone on which the nursing-rounds start operation has been performed, from the nurse mobile phone table storage unit and the assigned nurse table storage unit. Then, from among the hospitalized patients, the distance measurement unit may sequentially select hospitalized patients of the nurse call slave devices that are distant by a predetermined first distance or less from the nurse mobile phone on which the nursing-rounds start operation has been performed.

The location management server may include a map information storage unit for allowing the distance measurement unit to measure a distance on a movement line for actual movement in the hospital ward. The distance measurement unit may measure a distance, on the movement line, over which a nurse carrying the nurse mobile phone on which the nursing-rounds start operation has been performed moves to reach a location of the nurse call slave device, based on data in the map information storage unit, when measuring a distance between the nurse call slave device and the nurse mobile phone.

In such a configuration, the distance between the nurse call slave device and the nurse mobile phone is measured based on an actual distance over which the nurse moves to reach the location of the nurse call slave device, and the hospitalized patients are sequentially selected. Therefore, in a case where a hospitalized patient associated with the nurse call slave device does not satisfy the predetermined condition when the actual distance is used, or a hospitalized patient is distant from the nurse mobile phone by a distance longer than the predetermined first distance since, for example, the nurse mobile phone is on the upper floor or lower floor although the distance in the straight line therebetween is short, the hospitalized patient can be prevented from being selected.

A hospital room camera capable of taking a video image of a hospitalized patient on a bed, and a video analyzing unit capable of detecting a bed leaving state in which a hospitalized patient is not on a bed, based on the video image taken by the hospital room camera may be further provided. When, while the video analyzing unit detects the bed leaving state, the nursing-rounds start operation is performed from the nurse mobile phone of a nurse associated with the hospitalized patient in the bed leaving state, and the hospitalized patient detected to be in the bed leaving state is selected by the location management server, the control unit may perform control to transmit the nursing-rounds start signal to the hospitalized patient mobile phone of the hospitalized patient.

In the nurse call system having such a configuration, when a hospitalized patient selected by the location management server is not on the bed, the nursing-rounds start signal is transmitted to the hospitalized patient mobile phone of the hospitalized patient. Therefore, also in a case where the hospitalized patient who is carrying the hospitalized patient mobile phone is outside the hospital room, the hospitalized patient can be notified that the nursing rounds have started. Thus, the hospitalized patient can prepare for the nursing rounds by, for example, returning to the hospital room.

After the distance measurement unit selects a hospitalized patient who is distant from the nurse mobile phone by the first distance or less, when a distance between the nurse mobile phone and the nurse call slave device of the selected hospitalized patient becomes less than or equal to a predetermined second distance shorter than the first distance, notification that the hospitalized patient is distant from the nurse mobile phone by the second distance or less may be made to the control unit. Then, the control unit may perform control to further transmit, when receiving notification of the hospitalized patient who is distant by the second distance or less, an approach notification signal to the device of the hospitalized patient. The device that has received the approach notification signal may be controlled to make notification that a nurse will soon visit the hospital room.

In the nurse call system having such a configuration, the hospitalized patient can be notified that the nurse will soon visit the hospital room, and the hospitalized patient can further prepare for the nursing rounds without, for example, leaving the bed.

When the control unit is notified by the location management server that a hospitalized patient is distant from the nurse mobile phone by the second distance or less while the bed leaving state is detected by the video analyzing unit, the control unit may perform control to transmit the approach notification signal to the hospitalized patient mobile phone of the hospitalized patient.

In such a configuration, when a hospitalized patient is not on the bed, the approach notification signal is transmitted to the hospitalized patient mobile phone of the hospitalized patient. Therefore, in a case where the hospitalized patient who is carrying the hospitalized patient mobile phone is outside the hospital room, the hospitalized patient can be notified that a nurse will soon visit the hospital room. Thus, the hospitalized patient can prepare for the nursing rounds by, for example, quickly returning to the hospital room.

The control unit may perform control to also transmit location information of the nurse mobile phone to the device to which the approach notification signal has been transmitted. The device that has received the approach notification signal and the location information of the nurse mobile phone may be controlled to make notification for a location of the nurse mobile phone.

In the nurse call system having such a configuration, the hospitalized patient can specifically know the present location of the nurse.

An electronic key may be mounted to a door of the hospital room. The control unit may perform control to unlock the electronic key when a distance between the nurse mobile phone and the nurse call slave device is less than or equal to a predetermined third distance.

In the nurse call system having such a configuration, in a case where a distance between the nurse mobile phone and the nurse call slave device is less than or equal to a predetermined third distance, the electronic key of the hospital room of the hospitalized patient to whom a nurse who performs the nursing rounds is assigned is automatically unlocked. Therefore, the load and time, for the nurse, of unlocking the door of the hospital room can be eliminated, and the working efficiency of the nurse can be enhanced.

The predetermined third distance may be shorter than the second distance or may be longer than the second distance. In a case where the third distance is equal to the first distance or the second distance, the key may be unlocked when the nursing-rounds start signal or the approach notification signal is transmitted.

A nurse call system according to a second aspect of the present invention includes a nurse call slave device, a nurse call master device, a plate slave device, a bedside monitor, a corridor light, a control unit, and a plurality of nurse mobile phones. The nurse call slave device is provided for each bed in a hospital room for allowing a hospitalized patient to call a nurse. The nurse call master device is provided at a nurse station for answering a call from the nurse call slave device. The plate slave device, to which the nurse call slave device is connected, is provided near a bed in the hospital room. The bedside monitor is provided for each bed in the hospital room and is capable of displaying patient-related information. The corridor light is provided in front of the hospital room for indicating a call from the nurse call slave device. The control unit is configured to control calling and speaking, and communication between devices. The plurality of nurse mobile phones are carried by nurses for answering a call from the nurse call slave device. The plate slave device, the corridor light, or the control unit has an automatic answering unit for automatically answering a call from the nurse call slave device, and causes the automatic answering unit to automatically answer at least a part of calls from the nurse call slave device without calling the nurse call master device and the nurse mobile phones.

In the nurse call system having such a configuration, at least a part of calls from the nurse call slave devices is primarily answered automatically by the automatic answering unit without calling the nurse call master device and the nurse mobile phone, thereby reducing load of nursing work caused by the insufficient number of nurses.

The plate slave device, the corridor light, or the control unit may perform control to call the nurse call master device or the nurse mobile phones without answering performed automatically by the automatic answering unit when a predetermined urgent call occurs.

In the nurse call system having such a configuration, in the case of a call, such as a staff call, a call for toilet, or a bath call, which requires a matter to be highly urgently handled by nursing work, the nurse call master device or the nurse mobile phone can be immediately called without answering performed automatically by the automatic answering unit.

The automatic answering unit may include a keyword storage unit for storing a first keyword group including a plurality of keywords indicating a wrong call, and a sound recognition unit. In a case where, when a call from the nurse call slave device has been automatically answered, a content in the call includes the first keyword group, a hospitalized patient who has made the call through the nurse call slave device may be allowed to confirm whether or not the call from the nurse call slave device is to be cancelled, by using a sound or character information, through at least one device among the nurse call slave device, the plate slave device, and the bedside monitor of the hospitalized patient. The call from the nurse call slave device may be controlled to be cancelled when the hospitalized patient makes, through the device, a response indicating that the call from the nurse call slave device is to be cancelled, by using the sound or character information.

In such a configuration, in a case where a call from the nurse call slave device is a wrong call caused by, for example, an erroneous operation, the call from the nurse call slave device can be canceled before the nurse call master device or the nurse mobile phone is called. Therefore, an unnecessary call can be eliminated to reduce load of the nursing work.

The nurse call system may include a nurse mobile phone table storage unit in which a nurse and each nurse mobile phone are associated with each other, and an assigned nurse table storage unit in which a nurse and a hospitalized patient are associated with each other. The keyword storage unit may further store a second keyword group indicating that handling by an assigned nurse is required. In a case where, when a call from the nurse call slave device has been automatically answered, a content in the call includes the second keyword group, the automatic answering unit may be controlled to call the nurse mobile phone of a nurse associated with a hospitalized patient that has made the call from the nurse call slave device.

In the nurse call system having such a configuration, in a case where a call requires handling by an assigned nurse, the assigned nurse can be called. Thus, the call can be performed according to the content in the call.

The keyword storage unit of the nurse call system may further store a third keyword group indicating that highly urgent handling is not required. In a case where, when a call from the nurse call slave device has been automatically answered, a content in the call includes the third keyword group, the automatic answering unit may be controlled to transmit a message indicating the content in the call from a hospitalized patient who has made the call from the nurse call slave device, to the nurse mobile phone of a nurse associated with the hospitalized patient.

In the nurse call system having such a configuration, in the case of a call that requires handling by the assigned nurse but does not require immediate visiting, a message indicating the content of the call is merely transmitted without calling the nurse mobile phone of the assigned nurse, thereby reducing load of nursing work for answering the call.

In the nurse call system according to the second aspect of the present invention, a location information transmitter for wirelessly transmitting a location signal may be disposed at an appropriate place in a hospital ward, and a location management server for storing location information of each of the nurse mobile phones may be provided. Each nurse mobile phone may include a location information communication unit for receiving the location signal transmitted by the location information transmitter, and transmitting the location signal with an ID of the nurse mobile phone added thereto. The location management server may include a nurse mobile phone location storage unit, a bed location storage unit, and a distance measurement unit. The nurse mobile phone location storage unit stores the location information received from each nurse mobile phone. The bed location storage unit stores a location of the individual nurse call slave device. The distance measurement unit measures a distance between each nurse mobile phone and the nurse call slave device that has made a call, and selects the nurse mobile phone that satisfies a predetermined condition including the distance. The keyword storage unit may further store a fourth keyword group indicating that handling by a nurse is required. In a case where, when a call from the nurse call slave device has been automatically answered, a content in the call includes the fourth keyword group, the automatic answering unit may be controlled to cause the distance measurement unit to select the nurse mobile phone near the nurse call slave device, and call the selected nurse mobile phone.

In the nurse call system having such a configuration, in the case of a call that requires handling by any nurse including the assigned nurse and other nurses, the nurse mobile phone of the assigned nurse or another nurse who is near the nurse call slave device that has made the call can be called, and the calling can be performed according to the content in the call.

Meanwhile, in the nurse call system, the location information transmitter for wirelessly transmitting a location signal may be disposed at an appropriate place in a hospital ward, and the location management server for storing location information of each of the nurse mobile phones may be provided. Each nurse mobile phone may include the location information communication unit for receiving the location signal transmitted by the location information transmitter, and transmitting the location signal with an ID of the nurse mobile phone added thereto. The location management server may include the nurse mobile phone location storage unit, the bed location storage unit, and the distance measurement unit. The nurse mobile phone location storage unit stores the location information received from each nurse mobile phone. The bed location storage unit stores a location of the individual nurse call slave device. The distance measurement unit measures a distance between each nurse mobile phone and the nurse call slave device that has made a call, and selects the nurse mobile phone that satisfies the predetermined condition including the distance. In a case where, when a call from the nurse call slave device has been automatically answered, a content in the call does not include any of the first keyword group to the third keyword group, the automatic answering unit may be controlled to cause the distance measurement unit to select the nurse mobile phone near the nurse call slave device, and call the selected nurse mobile phone.

Also in the nurse call system having such a configuration, in the case of a call other than, for example, a call that requires handling by the assigned nurse, the nurse mobile phone of the assigned nurse or another nurse who is near the nurse call slave device that has made the call, can be called, and calling can be performed according to the content in the call.

A nurse call system according to a third aspect of the present invention includes a nurse call slave device, a nurse call master device, a plate slave device, a bedside monitor, a control unit, a plurality of nurse mobile phones, a plurality of hospitalized patient mobile phones. The nurse call slave device is provided for each bed in a hospital room for allowing a hospitalized patient to call a nurse. The nurse call master device is provided at a nurse station for answering a call from the nurse call slave device. The plate slave device, to which the nurse call slave device is connected, is provided near a bed in the hospital room. The bedside monitor is provided for each bed in the hospital room and is capable of displaying patient-related information. The control unit is configured to control calling and speaking, and communication between devices. The plurality of nurse mobile phones are carried by nurses for answering a call from the nurse call slave device. The plurality of hospitalized patient mobile phones are carried by hospitalized patients. One of devices from among the nurse call slave device, the plate slave device, the bedside monitor, and the hospitalized patient mobile phone includes a vital sign measurement unit or a vital sign communication unit. The vital sign measurement unit is capable of measuring a vital sign of the hospitalized patient by a predetermined body portion of the hospitalized patient touching the vital sign measurement unit. The vital sign communication unit is capable of obtaining vital sign information from a device for measuring the vital sign. Vital sign information obtained through measurement by the vital sign measurement unit or the vital sign information obtained by the vital sign communication unit is controlled to be transmitted together with predetermined patient information to the control unit.

In the nurse call system having such a configuration, the hospitalized patient can measure her/his vital signs and, and both the information of the measured vital signs and the predetermined patient information are transmitted to the control unit. Therefore, the assigned nurse need not measure the vital signs of the hospitalized patient several times a day, thereby reducing load of the nursing work.

One of the nurse call slave device, the plate slave device, the bedside monitor, and the hospitalized patient mobile phone may be controlled to perform personal authentication when the vital sign is measured.

In the nurse call system having such a configuration, when the vital sign is measured, the personal authentication is performed. Therefore, a person who measures the vital sign can be authenticated as the hospitalized patient him/herself, and the vital sign can then be measured.

The device that performs personal authentication may be the same as or different from the device that has the vital sign measurement unit.

The control unit may transmit a vital sign measurement request signal to the one of the devices which has the vital sign measurement unit or the vital sign communication unit at a predetermined preset time. The one of the devices which has received the vital sign measurement request signal may be controlled to instruct the hospitalized patient to measure a vital sign.

In the nurse call system having such a configuration, a hospitalized patient can be instructed to measure a vital sign at a predetermined preset time, whereby a request for measuring a vital sign can be regularly made to the hospitalized patient.

When the one of the devices which has received the vital sign measurement request signal has the vital sign measurement unit, the vital sign measurement unit may be controlled to be enabled, and the hospitalized patient may be instructed to measure a vital sign.

In such a configuration, in a case where any one of the devices has the vital sign measurement unit, the vital sign measurement unit can be enabled only when the vital sign needs to be measured.

When the vital sign information is not received from the one of the devices which has the vital sign measurement unit or the vital sign communication unit after elapse of a predetermined time since the vital sign measurement request signal has been transmitted to the one of the devices, the control unit may perform control to transmit a non-receipt-of-vital-sign-information notification signal to the nurse mobile phone of an assigned nurse.

In the nurse call system having such a configuration, the assigned nurse can be notified that the vital sign has not been measured by the hospitalized patient in a predetermined time period, so that the assigned nurse can perform handling as appropriate by, for example, visiting the hospital room of the hospitalized patient.

When the vital sign information is not received from the one of the devices which has the vital sign measurement unit or the vital sign communication unit after elapse of a predetermined time since the vital sign measurement request signal has been transmitted to the one of the devices, the control unit may perform control to transmit again the vital sign measurement request signal to the one of the devices.

In the nurse call system having such a configuration, in a case where the vital sign cannot be measured in a state where, for example, the hospitalized patient is in the toilet or is temporarily outside the hospital room, the hospitalized patient can be instructed again to measure the vital sign.

Each nurse mobile phone or the nurse call master device may be structured to transmit the vital sign measurement request signal to the one of the devices which has the vital sign measurement unit or the vital sign communication unit.

In the nurse call system having such a configuration, in a case where, for example, a vital sign has not been measured by the hospitalized patient in a predetermined time period, the vital sign measurement request signal can be transmitted at a time, other than the predetermined timing which is preset in the control unit, when the assigned nurse determines that the vital sign measurement request signal is to be transmitted.

A nurse call system according to a fourth aspect of the present invention includes a nurse call slave device, a nurse call master device, a plate slave device, a bedside monitor, a plurality of nurse mobile phones, a hospital room camera, a control unit. The nurse call slave device is provided for each bed in a hospital room for allowing a hospitalized patient to call a nurse. The nurse call master device is provided at a nurse station for answering a call from the nurse call slave device. The plate slave device, to which the nurse call slave device is connected, is provided near a bed in the hospital room. The bedside monitor is provided for each bed in the hospital room and is capable of displaying patient-related information. The plurality of nurse mobile phones are carried by nurses for answering a call from the nurse call slave device. The hospital room camera is capable of taking an image of a hospitalized patient on a bed. The control unit is configured to control calling and speaking, and communication between devices. In the nurse call system, at least one of devices among the nurse call master device and each nurse mobile phone has a watching start unit for starting watching by a nurse. In response to a watching start operation from the one of the devices which has the watching start unit, the control unit performs control to start up the hospital room camera associated with a hospitalized patient registered as a hospitalized patient for whom watching is to be performed, and transmit an image taken by the hospital room camera to the device on which the watching start operation has been performed.

In the nurse call system having such a configuration, a nurse or the like performs the watching start operation from the nurse call master device or the nurse mobile phone having the watching start unit, whereby the hospital room camera is started up and the image taken by the hospital room camera is transmitted to the nurse call master device or the nurse mobile phone on which the watching start operation has been performed. On the nurse call master device or the nurse mobile phone on which the watching start operation has been performed, a nurse is allowed to confirm the image taken by the hospital room camera, to confirm the state of the hospitalized patient. Therefore, the necessary number of times the assigned nurse visits the hospital room of the hospitalized patient in one day can be reduced, thereby reducing load of the nursing work.

The one of the devices which has the watching start unit may be configured to communicate through a call with any one of the hospital room camera, the nurse call slave device, the plate slave device, and the bedside monitor while the hospital room camera is in operation by start-up performed in the watching start operation.

In the nurse call system having such a configuration, a nurse can talk with the hospitalized patient while confirming the state of the hospitalized patient through the nurse call master device or the nurse mobile phone, so that the nurse can confirm the physical condition and the like, and can more correctly recognize the state of the hospitalized patient.

When the watching start operation is performed from the one of the devices which has the watching start unit, before the hospital room camera is started up to start taking an image, the control unit may perform control to cause any one of the hospital room camera, the nurse call slave device, the plate slave device, and the bedside monitor to notify the hospitalized patient that watching start.

In the nurse call system having such a configuration, the hospitalized patient can be notified that the watching using the hospital room camera start, thereby enhancing the privacy of the hospitalized patient.

One of devices from among the hospital room camera, the nurse call slave device, the plate slave device, and the bedside monitor may have a watching allowing unit for allowing the hospital room camera to start up according to the watching start operation. The control unit may perform control to start up the hospital room camera when a watching allowing operation is performed by the hospitalized patient who has been notified, by the one of the devices which has the watching allowing unit, that watching start.

In the nurse call system having such a configuration, in a case where a hospitalized patient performs the watching allowing operation, the hospital room camera is started up, thereby further enhancing the privacy of the hospitalized patient.

A vital sign information obtaining unit and a state determination unit may be further provided. The vital sign information obtaining unit is configured to obtain vital sign information of the hospitalized patient. The state determination unit is configured to determine whether or not a hospitalized patient is asleep, based on the vital sign information obtained by the vital sign information obtaining unit. The control unit may perform control to start up the hospital room camera even when the hospitalized patient does not perform the watching allowing operation in a case where the state determination unit determines that the hospitalized patient is asleep.

In the nurse call system having such a configuration, the watching can be smoothly performed in a case where the hospitalized patient is asleep.

The control unit may perform control to start up the hospital room camera in a predetermined time range even when the hospitalized patient does not perform the watching allowing operation.

The predetermined time range may be set to any time range. For example, the predetermined time range may be set to a time range from lights out to the morning, for example, from 10 p.m. to 7 a.m. In the nurse call system having such a configuration, the watching can be smoothly performed in a time range in which most of the hospitalized patients are assumed to be asleep.

A nurse call system according to a fifth aspect of the present invention includes a nurse call slave device, a nurse call master device, a plate slave device, a bedside monitor, a control unit, a plurality of nurse mobile phones, a nurse call server, and a sound analyzing unit. The nurse call slave device is provided for each bed in a hospital room for allowing a hospitalized patient to call a nurse. The nurse call master device is provided at a nurse station for answering a call from the nurse call slave device. The plate slave device, to which the nurse call slave device is connected, is provided near a bed in the hospital room. The bedside monitor is provided for each bed in the hospital room and is capable of displaying patient-related information. The control unit is configured to control calling and speaking, and communication between devices. The plurality of nurse mobile phones are carried by nurses for answering a call from the nurse call slave device. The nurse call server has a nursing record storage unit. The sound analyzing unit recognizes at least a specific word from a sound. At least one of the nurse call slave device, the plate slave device, the bedside monitor, and each nurse mobile phone is an analysis allowing device for which the sound analyzing unit performs sound analysis. The control unit performs control to shift a mode to a nursing records input mode when the specific word has been recognized from the sound analyzed by the sound analyzing unit, and to start input of nursing records to the nurse call server. The sound analyzing unit then recognizes a nursing word inputted as a sound from the analysis allowing device, input of nursing records as a sound is performed, and the nursing records inputted as the sound are stored in the nurse call server.

In this configuration, the nursing records can be inputted from a hospital room of a patient for whom the treatment has been performed. Furthermore, the input can be made as a sound, thereby substantially reducing load of nursing work for inputting the nursing records.

The analysis allowing device may be the bedside monitor.

In this configuration, the bedside monitor is disposed near a hand, and input can be more easily performed to the bedside monitor as compared with, for example, the plate slave device disposed on the wall surface. The bedside monitor is associated with the nurse call slave device (bed) unlike the nurse mobile phone. Therefore, a patient for whom the input is performed can be recognized from the bedside monitor ID, and information for recognizing a patient for whom the nursing records are inputted need not be inputted together, and input can be performed through a simple operation.

The sound analyzing unit may be provided in at least one of the control unit, the nurse call server, and a cloud service.

In this configuration, the sound analyzing unit is provided in at least one of the control unit, the nurse call server, and a cloud service, whereby the sound analyzing unit need not be provided for each bed or for each hospital room, thereby preventing increase of cost for the bedside monitor, the plate slave device, or the like.

At least one of the bedside monitor and each nurse mobile phone may display the nursing records recorded as the sound in response to a predetermined display operation.

In this configuration, the inputted nursing records can be confirmed at the location where the input has been performed, and the nurse who has performed the input operation can feel reassured.

The present invention can provide a nurse call system that reduces load of nursing work on nurses, more specifically, a nurse call system that can notify a hospitalized patient that her/his assigned nurse has started nursing rounds, a nurse call system that does not immediately call a nurse call master device or the like for at least a part of calls from nurse call slave devices, a nurse call system that allows hospitalized patients to measure vital signs by themselves, a nurse call system that allows nurses to confirm the state of hospitalized patients without visiting the hospital rooms, and a nurse call system that facilitates input of nursing records.

DETAILED DESCRIPTION OF THE INVENTION

Hereinafter, preferred embodiments of a nurse call system according to the disclosure will be described in detail with reference to the drawings.

A first embodiment of the present invention is described below.

Figure 1:
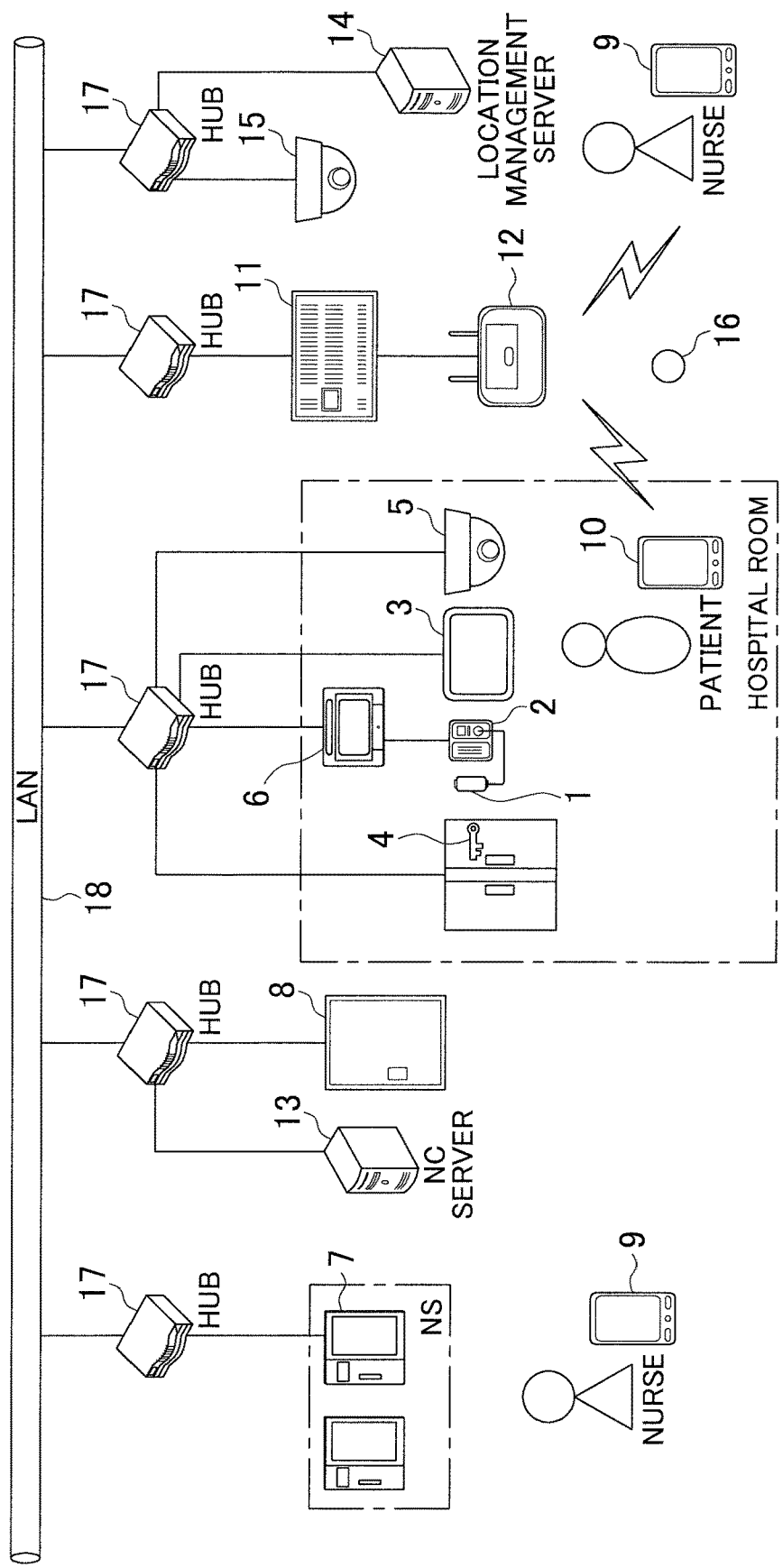
FIG. 1 illustrates the entire configuration of a nurse call system.

FIG. 1 illustrates a configuration of a nurse call system according to the first embodiment of the present invention.

As shown in FIG. 1, the nurse call system includes a nurse call slave device 1, a plate slave device 2, a bedside monitor 3, an electronic key 4, a hospital room camera 5, a corridor light 6, a nurse call master device 7, a controller 8, a nurse mobile phone 9, and a hospitalized patient mobile phone 10. The nurse call slave device 1 is provided for each bed in a hospital room for allowing a hospitalized patient to call a nurse. To the plate slave device 2, the nurse call slave device 1 is connected, and the plate slave device 2 is provided on a wall surface near the bed in the hospital room. The bedside monitor 3 is provided for each bed in the hospital room and is capable of displaying patient-related information. The electronic key 4 is disposed at a door of the hospital room. The hospital room camera 5 is capable of taking an image of a hospitalized patient on a bed. The corridor light 6 is provided on a corridor wall surface near the hospital room. The nurse call master device 1 is provided at a nurse station for answering a call from the nurse call slave device 1. The controller 8 controls the devices such as the nurse call slave device 1, the corridor light 6, and the nurse call master device 7. The nurse mobile phone 9 is carried by a nurse. The hospitalized patient mobile phone 10 is carried by a hospitalized patient.

The nurse call system includes an exchange device (hereinafter, referred to as IP-PBX) 11 which is connected to the controller 8 for managing communication with the nurse mobile phone 9 or the hospitalized patient mobile phone 10, and a base station 12 that allows wireless communication between the IP-PBX 11 and the nurse mobile phone 9 or the hospitalized patient mobile phone 10. The nurse call system further includes a nurse call server 13 for storing various data about the hospitalized patients, a location management server 14 for managing location information of nurses, a common area camera 15 disposed at a common area, and an indoor messaging system (IMES) transmitter 16.

The plate slave device 2, to which the nurse call slave device 1 is connected, is connected to the corridor light 6 via a transmission line. The bedside monitor 3, the electronic key 4, the hospital room camera 5, the nurse call master device 7, the controller 8, the corridor light 6, the IP-PBX 11, the nurse call server 13, the location management server 14, and the common area camera 15 are connected via HUBs 17 to a LAN 18 provided in the hospital.

The IP-PBX 11 is connected to the base station 12 via a transmission line.

The base stations 12 are disposed at a plurality of locations in the facilities as appropriate.

Figure 2:
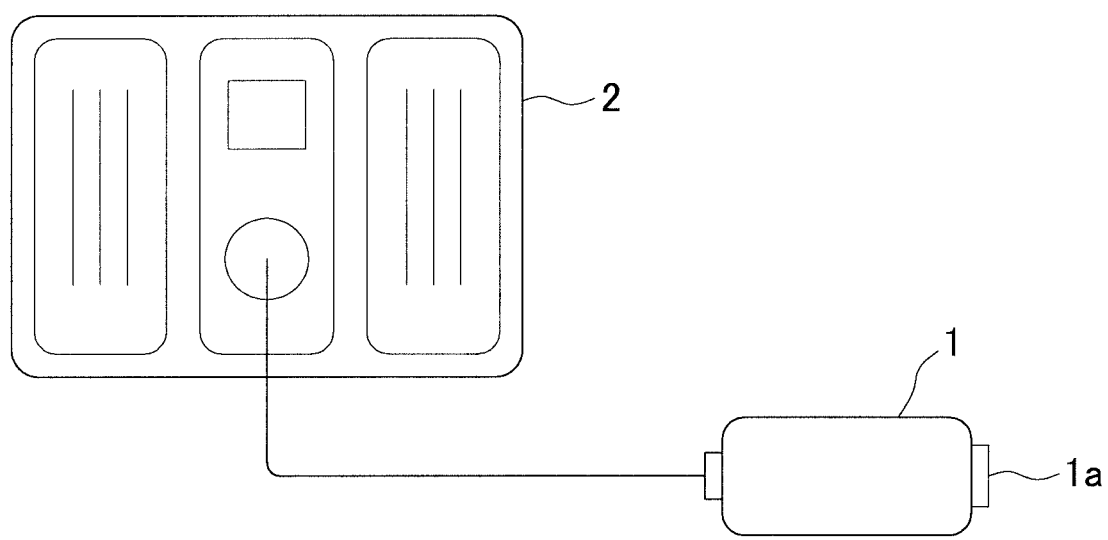
FIG. 2 illustrates a nurse call slave device 1 and a plate slave device 2 of the nurse call system.

As shown in FIG. 2, the nurse call slave device 1 has a call button 1a for calling a nurse, and is connected to the plate slave device 2.

Figure 3:
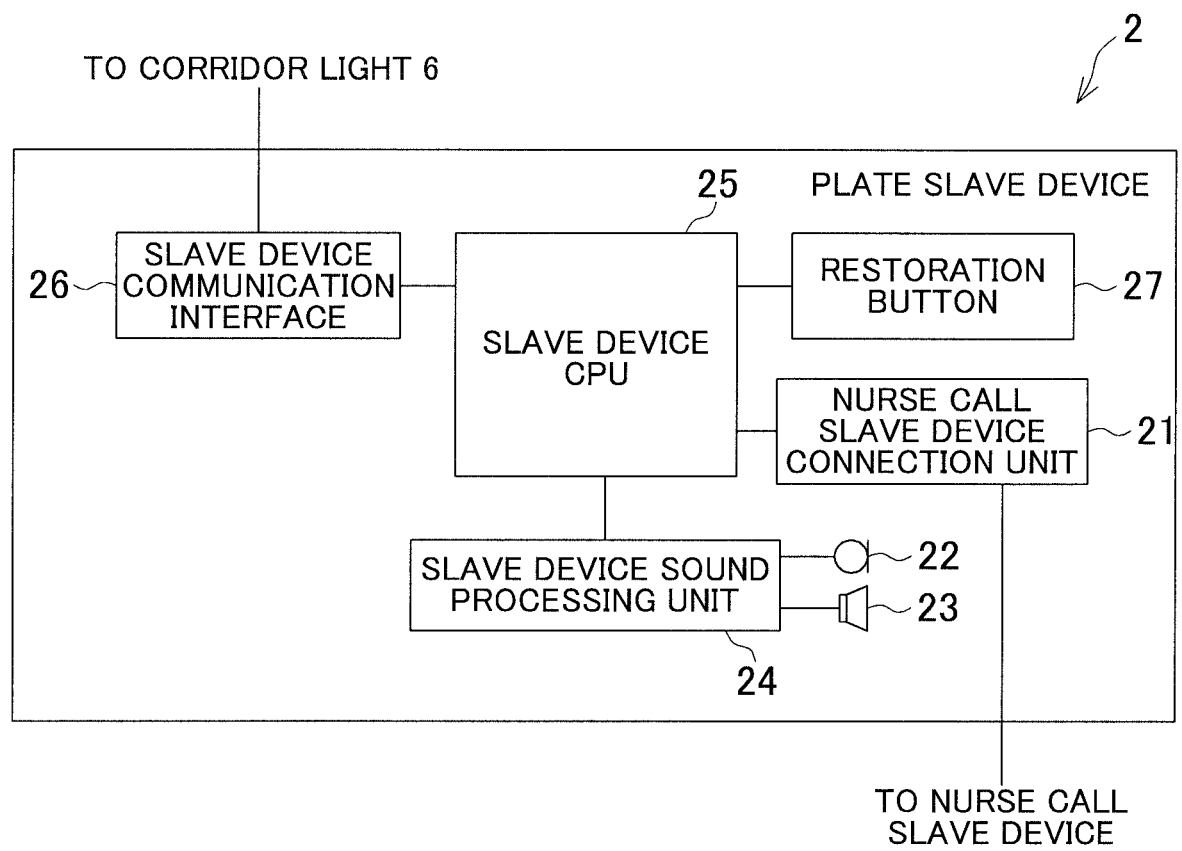
FIG. 3 is a functional block diagram illustrating a configuration of the plate slave device 2 of the nurse call system.

As shown in FIG. 3, the plate slave device 2 includes a nurse call slave device connection unit 21 for making connection to the nurse call slave device 1, a microphone 22 and a loudspeaker 23 for speaking, and a slave device sound processing unit 24 for processing a sound signal. The plate slave device 2 further includes a slave device CPU 25 for controlling the plate slave device 2, a slave device communication IF (interface) 26 for communicating with the corridor light 6, and a restoration button 27 capable of stopping a notification operation and the like.

Figure 4:
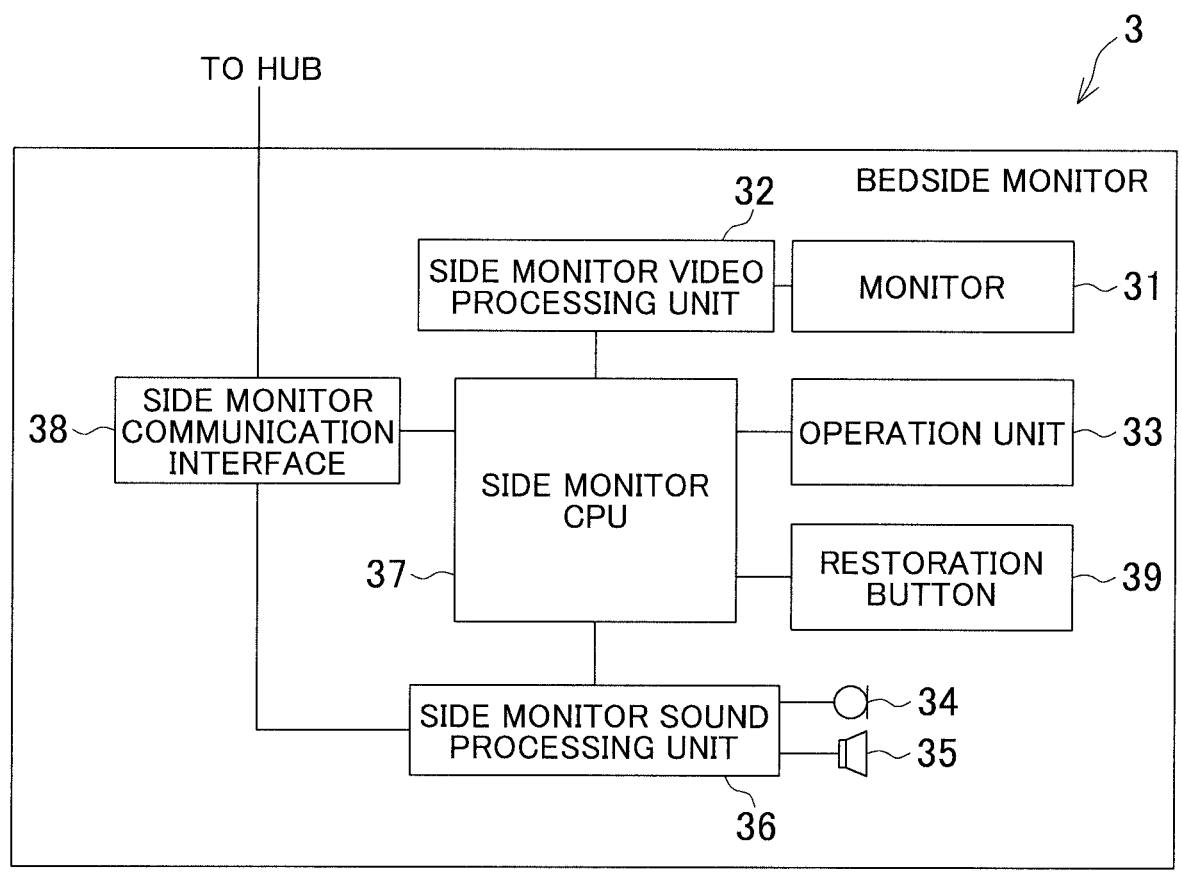
FIG. 4 is a functional block diagram illustrating a configuration of a bedside monitor 3 of the nurse call system.

As shown in FIG. 4, the bedside monitor 3 includes a monitor 31 for displaying various information, a side monitor video processing unit 32 for processing video images to be displayed on the monitor 31, an operation unit 33 that is implemented by a touch panel for performing various operations, a microphone 34 and a loudspeaker 35 for speaking, and a side monitor sound processing unit 36 for processing a sound signal. The bedside monitor 3 further includes a side monitor CPU 37 for controlling the bedside monitor 3, a side monitor communication IF 38 for communicating with the controller 8, and a restoration button 39 capable of performing operations such as stopping a notification operation and turning on/off a liquid crystal display.

The hospital room camera 5 includes a video analyzing unit for performing detection for a bed leaving state in which a hospitalized patient is not on the bed, based on the video image taken by the camera 5. In the video analyzing unit, a specific area is set in advance within the angle of view of the hospital room camera 5 for determination of bed leaving such that the specific area matches the bed that is an imaging target. The video analyzing unit determines whether or not the bed leaving has occurred, by detecting for a person moving out of the specific area.

Figure 5:
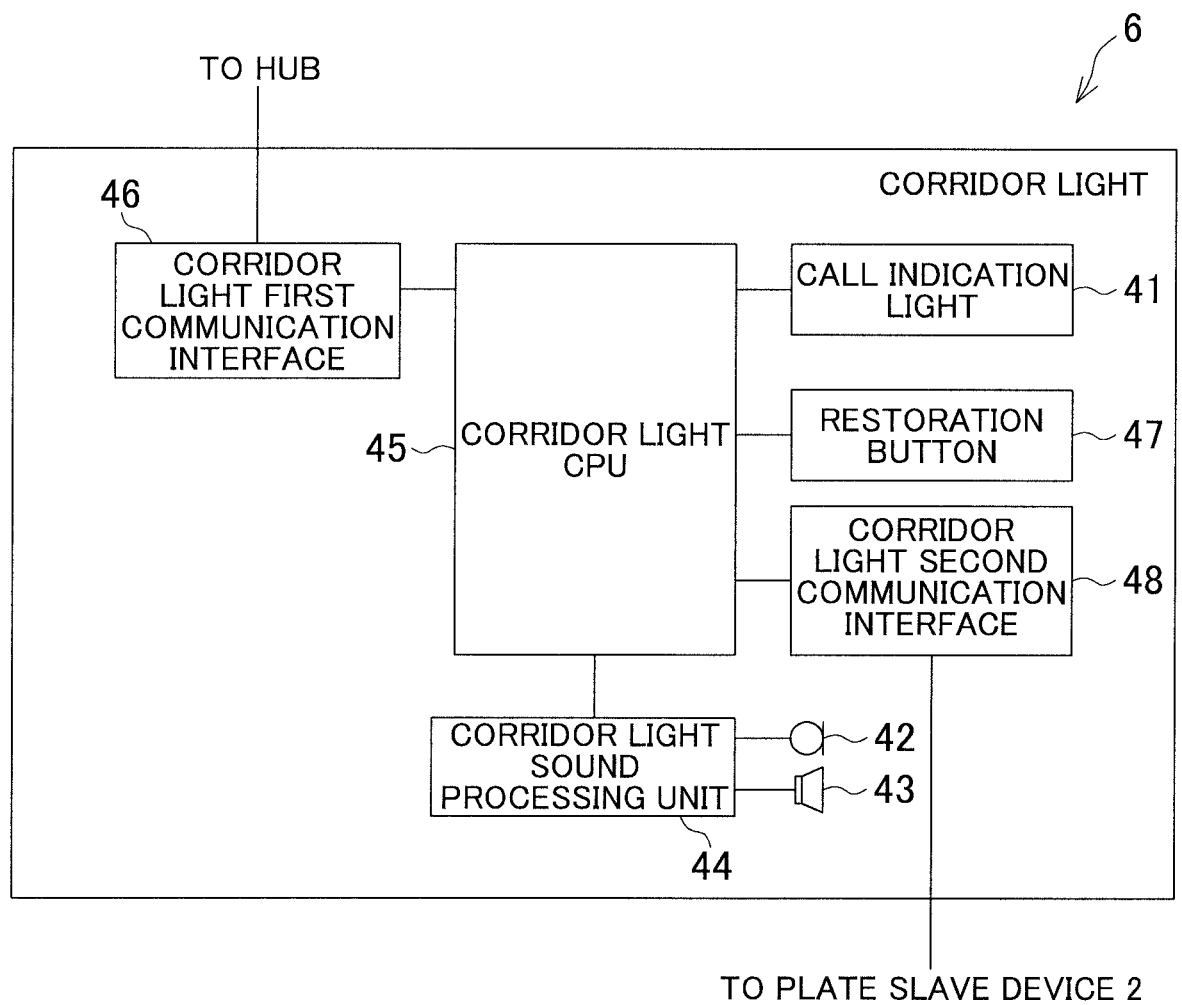
FIG. 5 is a functional block diagram illustrating a configuration of a corridor light 6 of the nurse call system.

As shown in FIG. 5, the corridor light 6 includes a call indication light 41 for indicating occurrence of a call from a hospitalized patient by light emission, a microphone 42 and a loudspeaker 43 for speaking, a corridor light sound processing unit 44 for processing a sound signal, and a corridor light CPU 45 for controlling the corridor light 6. The corridor light 6 further includes a corridor light first communication IF 46 for communicating with the nurse call master device 7 and the like, a restoration button 47 for stopping a notification operation, and a corridor light second communication IF 48 for communicating with the plate slave device 2.

Figure 6:
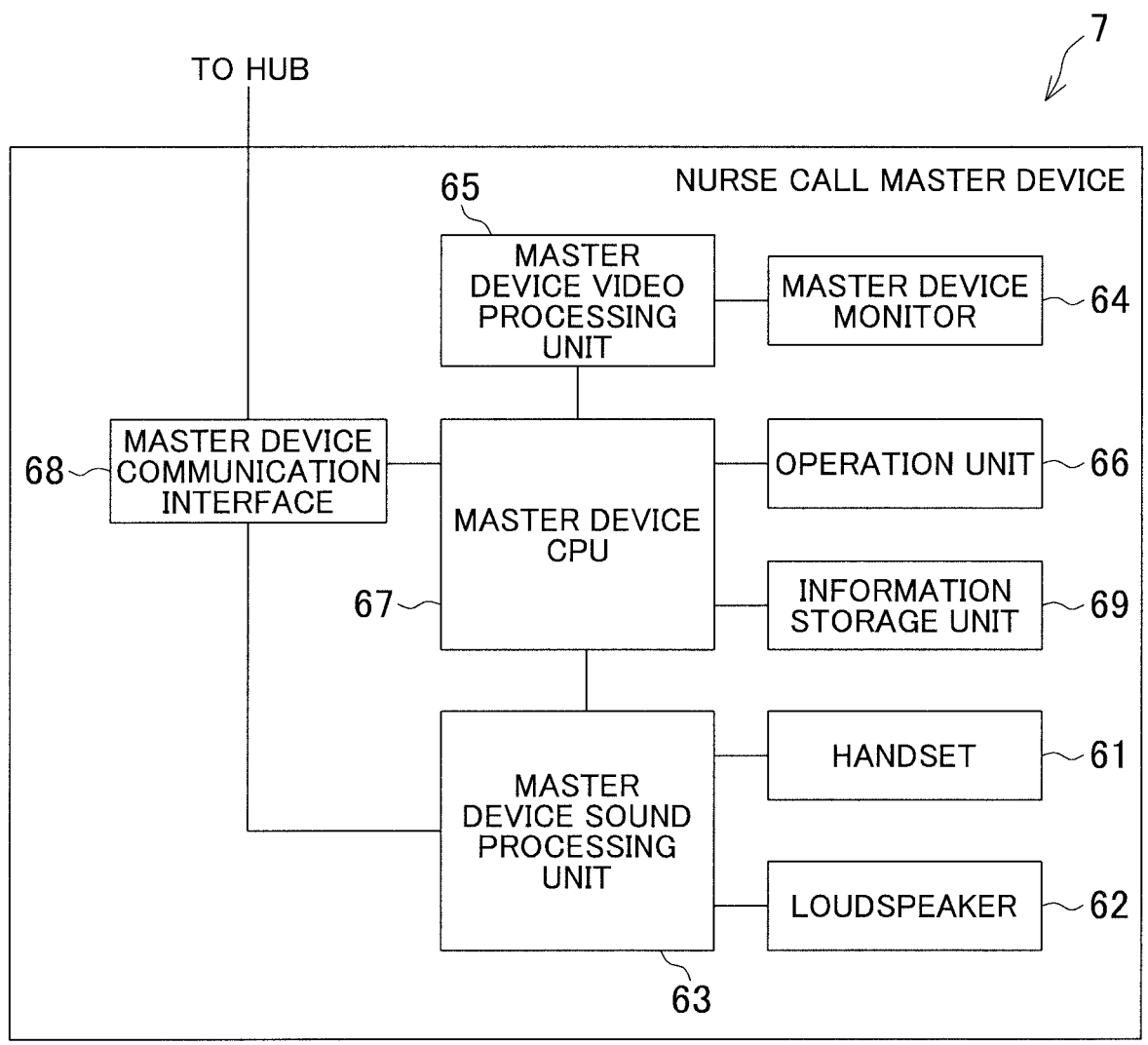
FIG. 6 is a functional block diagram illustrating a configuration of a nurse call master device 7 of the nurse call system.

As shown in FIG. 6, the nurse call master device 7 includes a handset 61 for answering a call from the nurse call slave device 1, a loudspeaker 62 for emitting an alarm sound and the like, a master device sound processing unit 63 for processing a sound signal and processing an alarm sound, a master device monitor 64 for displaying various information, and a master device video processing unit 65 for processing a video image to be displayed on the master device monitor 64. The nurse call master device 7 further includes an operation unit 66 that is implemented by a touch panel for performing various operations, a master device CPU 67 for controlling the entire nurse call master device 7, a master device communication IF 68 for communicating with another device such as the controller 8, and an information storage unit 69 for storing various information.

Figure 7:
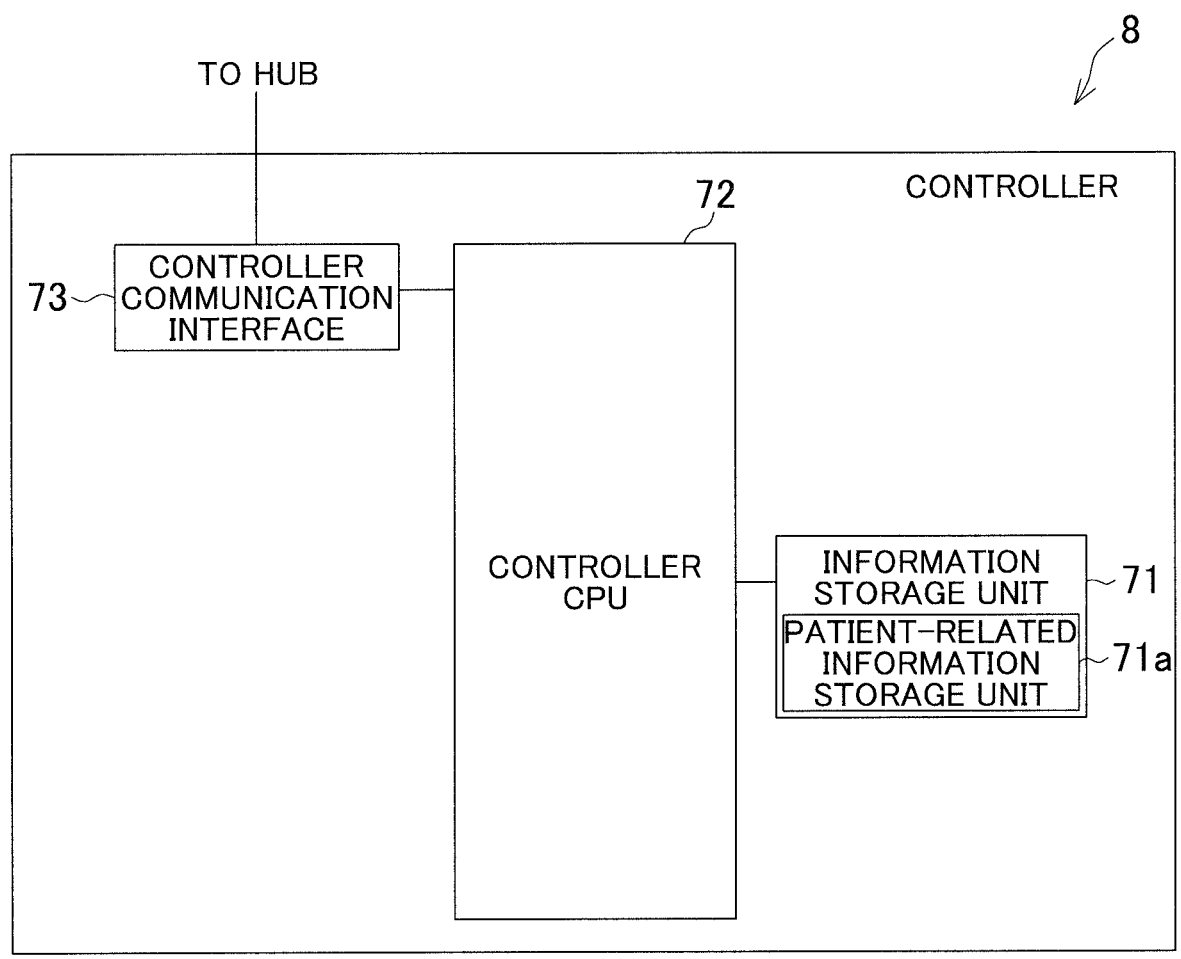
FIG. 7 is a functional block diagram illustrating a configuration of a controller 8 of the nurse call system.

As shown in FIG. 7, the controller 8 includes an information storage unit 71 for storing various information, a controller CPU 72 for controlling the controller 8, and a controller communication IF 73 for communicating with another device such as the corridor light 6.

The information storage unit 71 includes a patient-related information storage unit 71*a* for storing patient-related information. The patient-related information storage unit 71*a* stores patient information such as a name and an age of each hospitalized patient, nursing information such as a nursing classification and a medical specialty of each hospitalized patient, a relationship between the patient information and a slave device ID of the nurse call slave device 1, schedule information about examinations, surgeries, and the like of each hospitalized patient, mobile phone information about the hospitalized patient mobile phone 10 of each patient, and the like. Such information is inputted through operation on the nurse call master device 7.

Each of the nurse mobile phone 9 and the hospitalized patient mobile phone 10 is a multifunctional terminal having a mobile phone function. For example, a device called a smartphone can be used with predetermined application software installed thereon.

The nurse mobile phone 9 allows a nurse to answer a call from the nurse call slave device 1. The hospitalized patient mobile phone 10 can be set to receive a nursing-rounds start signal indicating that an assigned nurse has started nursing rounds as described below.

The nurse mobile phone 9 constitutes a location specifying system together with the IMES transmitter 16 and the location management server 14. Therefore, the nurse mobile phone 9 has, therein, a GPS communication unit (not shown) which specifies its own location by receiving satellite radio waves of a GPS and transmits the specified location information with its own ID added thereto.

Figure 8:
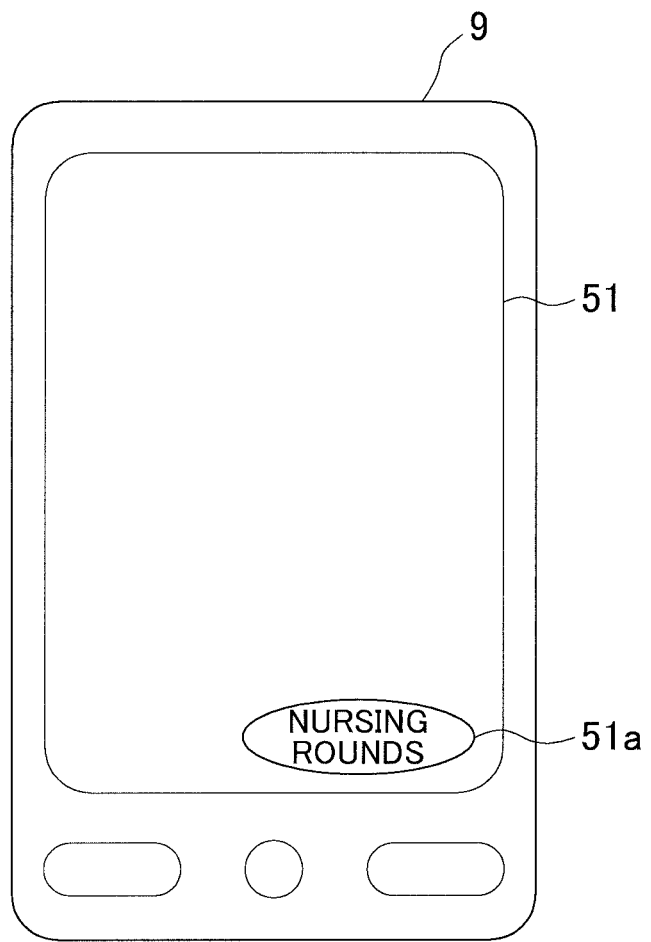
FIG. 8 illustrates a display screen of a nurse mobile phone 9.
Figure 9:
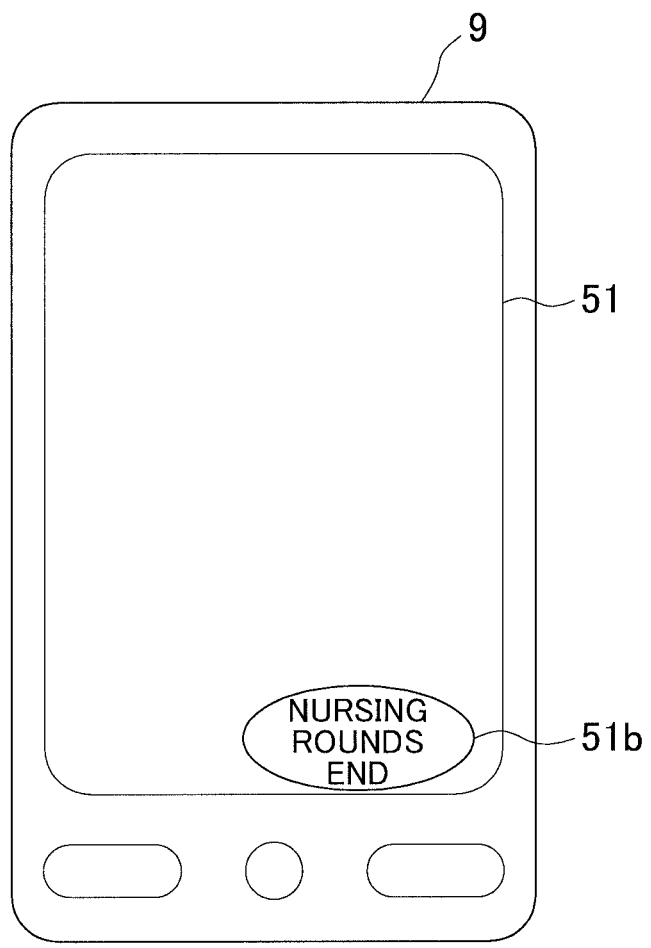
FIG. 9 illustrates a display screen of the nurse mobile phone 9.

As shown in FIG. 8, the nurse mobile phone 9 has a display unit 51 that is implemented by a touch panel, and displays a nursing-rounds start button 51*a* on the display unit 51 through a predetermined operation from a nurse. When the nursing-rounds start button 51*a* is touched, the nurse mobile phone 9 displays a nursing-rounds end button 51*b* on the display unit 51 as shown in FIG. 9. Furthermore, the operation as described below is performed according to the start of nursing rounds.

Figure 10:
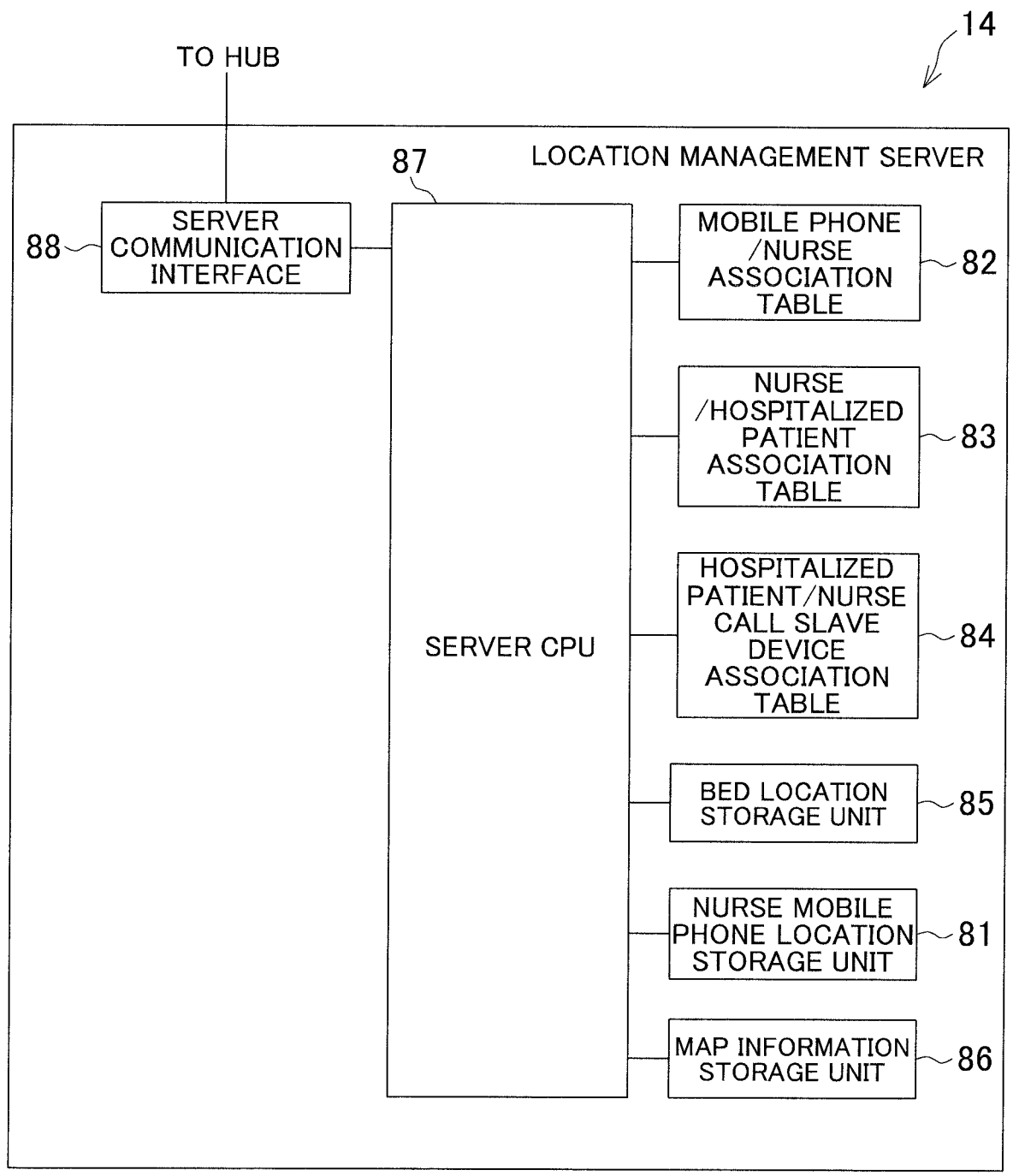
FIG. 10 is a functional block diagram illustrating a configuration of a location management server 14.

As shown in FIG. 10, the location management server 14 includes a nurse mobile phone location storage unit 81, a mobile phone/nurse association table (nurse mobile phone table storage unit) 82, a nurse/hospitalized patient association table (assigned nurse table storage unit) 83, a hospitalized patient/nurse call slave device association table (hospitalized patient table storage unit) 84, a bed location storage unit 85, a map information storage unit 86, a server CPU 87, and a server communication IF 88. The nurse mobile phone location storage unit 81 stores the location of each nurse mobile phone 9. The mobile phone/nurse association table 82 stores association between each nurse and the nurse mobile phone 9 carried by the nurse. The nurse/hospitalized patient association table 83 stores association between each nurse and a hospitalized patient. The hospitalized patient/nurse call slave device association table 84 stores association between each hospitalized patient and the nurse call slave device. The bed location storage unit 85 stores the location (bed location) of each nurse call slave device in a hospital ward. The map information storage unit 86 calculates a distance. The server CPU 87 controls update of the location information of the nurse mobile phone 9, controls selection of hospitalized patients to which the nursing-rounds start signal is to be transmitted, and further controls the entire location management server 14. The server communication IF 88 communicates with another device such as the controller 8.

The IMES transmitters 16 are provided at appropriate locations in the hospital ward or in the hospital, e.g., in each hospital room, the nurse station, an operating room, a waiting room, a dayroom, a corridor, and the like, and constantly transmit own location information by radio signals in the same radio wave format as the GPS radio waves.

The GPS communication unit provided in the nurse mobile phone 9 receives the location information transmitted from the near IMES transmitter 16 among the IMES transmitters 16, thereby recognizing its own location. The GPS communication unit regularly transmits the recognized location information with an ID added thereto, to the location management server 14. The location information transmitted by the nurse mobile phone 9 is received by the base station 12 as in the case of a normal speech signal, and then is transmitted via the exchange device 11 and the LAN 18 to the location management server 14, so as to be stored therein. Thus, the location specifying system for recognizing the present location of the nurse mobile phone 9 is established.

In a case where a call for a nurse is made by the nurse call slave device 1, the controller 8 causes the location management server 14 to select a nurse who is near the location of the nurse call slave device 1 of the hospitalized patient who has made the call, from among nurses associated with the hospitalized patient, with reference to the mobile phone/nurse association table 82 and the nurse/hospitalized patient association table 83. Then, the nurse mobile phone 9 of the nurse is notified that the call is made.

The common area cameras 15 are provided as appropriate in common areas in the hospital ward or in the hospital, such as a corridor on each floor, the waiting room, and a dayroom. Images taken by the common area cameras 15 and the hospital room camera 5 can be displayed on the master device monitor 64 through operation on the operation unit 66 of the nurse call master device 7.

The operation of the nurse call system having the above-described configuration will be described below.

Calling for a nurse from the nurse call slave device 1, sound notification operations of the nurse call master device 7 and the nurse mobile phone 9 which are called, and an answering operation of the nurse call master device 7 or the nurse mobile phone 9 are the same as in conventional art. Therefore, the description of such operations is omitted, and an operation performed when a nurse performs the nursing-rounds start operation from the nurse mobile phone 9 will be described herein. In the description herein, the nursing-rounds start signal is set to be usually transmitted to the bedside monitor 3.

As described above, the location information of each nurse mobile phone 9 is regularly transmitted to the location management server 14, and data in the nurse mobile phone location storage unit 81 is rewritten and saved with the latest data through control by the server CPU 87.

The hospital room camera 5 is constantly in operation.

When a nurse who intends to start nursing rounds touches the nursing-rounds start button 51*a* of the nurse mobile phone 9, the controller 8 causes the location management server 14 to sequentially select hospitalized patients to which the nursing-rounds start signal is to be transmitted.

The location management server 14 performs control as described below to sequentially select hospitalized patients who satisfy a predetermined preset condition, based on the location information of the nurse mobile phone 9 of the nurse who has performed the nursing-rounds start operation, and notify the controller 8 of the sequentially selected hospitalized patients. The hospitalized patients, who satisfy a predetermined condition that a distance between the nurse who has performed the nursing-rounds start operation and the nurse call slave device 1 of the hospitalized patient is less than or equal to 20 meters, are sequentially selected from among the hospitalized patients to whom the nurse is assigned.

With reference to the mobile phone/nurse association table 82 and the nurse/hospitalized patient association table 83, the server CPU 87 specifies the nurse mobile phone 9 from the mobile phone ID information received from the controller 8, specifies a nurse associated with the nurse mobile phone 9, and reads hospitalized patients associated with the nurse.

The nurse mobile phone location storage unit 81, the hospitalized patient/nurse call slave device association table 84, the bed location storage unit 85, and the map information storage unit 86 are used to read a location of the nurse call slave device 1 (bed) of each of the read hospitalized patients, select the hospitalized patients associated with the nurse call slave devices 1 each of which is distant from the location of the nurse mobile phone 9 on the movement line by 20 meters or less, and transmit the result to the controller 8.

The hospitalized patients are sequentially selected based on the latest data in the nurse mobile phone location storage unit 81 until the nursing-rounds end button 51*b* of the nurse mobile phone 9 is touched.

When the hospitalized patients have been selected by the location management server 14, the controller 8 determines whether or not the video analyzing unit of the hospital room camera 5 of each hospitalized patient detects a bed leaving state of the hospitalized patient.

When the bed leaving state is not detected, the controller 8 performs control to transmit the nursing-rounds start signal to the bedside monitor 3 of the hospitalized patient.

Meanwhile, when the bed leaving state is detected, the controller 8 performs control to read the mobile phone information 10 of the hospitalized patient from the patient-related information storage unit 71*a*, and transmit the nursing-rounds start signal to the hospitalized patient mobile phone 10 of the hospitalized patient.

The bedside monitor 3 or the hospitalized patient mobile phone 10 that has received the nursing-rounds start signal is controlled to make notification that the nursing rounds have started. Specifically, the bedside monitor 3 or the hospitalized patient mobile phone 10 displays a message such as "the nurse has started nursing rounds" for indicating that the nursing rounds have started.

In the present embodiment, notification of the start of the nursing rounds is made by display of the message. However, the present invention is not limited to the embodiment, and, for example, not only display of the message but also sound from the loudspeaker 35 or the like may be used to make notification for the location. Alternatively, the notification for the location may be made merely by sound.

After the hospitalized patients who are distant from the nurse mobile phone 9 by 20 meters or less are sequentially selected based on the location information of the nurse mobile phone 9 of the nurse who has performed the nursing-rounds start operation, and the nursing-rounds start signal is transmitted to each of the selected hospitalized patients, when the distance between the nurse call slave device 1 of the selected hospitalized patient and the nurse mobile phone 9 becomes shorter such that the distance is 10 meters, the server CPU 87 of the location management server 14 performs control to transmit, to the controller 8, the hospitalized patients who are distant from the nurse mobile phone 9 by 10 meters, and the present location information of the nurse mobile phone 9.

This control is also sequentially performed based on the latest data in the nurse mobile phone location storage unit 81 until the nursing-rounds end button 51*b* of the nurse mobile phone 9 is touched.

When the hospitalized patients have been selected by the location management server 14, the controller 8 performs control to transmit an approach notification signal together with the location information of the nurse mobile phone 9 to the bedside monitor 3 of each of the hospitalized patients.

The bedside monitor 3 that has received the approach notification signal is controlled to display the present location of the nurse and make notification that the nurse will visit the hospitalized patient soon. Specifically, a message such as "the nurse will soon visit the hospital room for nursing rounds" for making notification that the nurse will soon visit the hospital room, together with the present location of the nurse, is displayed on the bedside monitor 3.

The present location of the nurse may be displayed by using the map of the hospital, or by specifically indicating a hospital room number.

For example, the notification that the nurse will visit the hospital room may be made to the hospitalized patient by displaying the message together with notification, for the location, by a sound from the loudspeaker 35. Alternatively, the notification for the location may be made merely by sound.

When the distance between the nurse mobile phone 9 and the nurse call slave device 1 has become less than or equal to 5 meters, the controller 8 performs control to unlock the electronic key 4.

The above-described operation ends when the nurse has ended the nursing rounds and touches the nursing-rounds end button 51b of the nurse mobile phone 9.

Thus, in the nurse call system according to the first embodiment, in a case where the nursing-rounds start operation is performed from the nurse mobile phone 9, the controller 8 performs control to transmit the nursing-rounds start signal to the bedside monitor 3 of each of the hospitalized patients which are selected by the location management server 14. The bedside monitor 3 that has received the nursing-rounds start signal is controlled to make notification that the nursing rounds have started. Therefore, notification that the assigned nurse has started the nursing rounds can be made to the hospitalized patient. Thus, the hospitalized patient can prepare for the nursing rounds without freely leaving the hospital room, and, when the nurse visits the hospital room for the nursing rounds, the hospitalized patient is less likely to be absent, thereby enhancing efficiency of the nursing work.

Furthermore, the hospitalized patient is notified in advance that the nursing rounds have started, and is not suddenly visited by the nurse for the nursing rounds, thereby enhancing the privacy of the hospitalized patient.

In the present embodiment, the location management server 14 sequentially selects the hospitalized patients whose nurse call slave devices 1 are distant, by 20 meters or less, from the nurse who has performed the nursing-rounds start operation, from among the hospitalized patients to whom the nurse is assigned. However, the present invention is not limited to the embodiment, and the hospitalized patients who satisfy predetermined preset conditions including the distance may be sequentially selected.

For example, the hospitalized patients whose nurse call slave devices 1 are distant, by a predetermined first distance or less, from the nurse who has performed the nursing-rounds start operation, may be sequentially selected from among the hospitalized patients to whom the nurse is assigned.

The nursing rounds are sequentially performed from the hospitalized patient close to the assigned nurse, and the nurse measures vital signs of each hospitalized patient and performs interview with each hospitalized patient, so that it takes a long time to complete the nursing rounds in a case where the nurse is assigned to many hospitalized patients. Therefore, in a case where, when the nurse has performed the nursing-rounds start operation, the notification that the nursing rounds have started is simultaneously made to all the hospitalized patients to whom the nurse is assigned, the hospitalized patient, in a far hospital room, whose turn is later in the order of the nursing rounds may wait for the nursing rounds for a considerably long time after the hospitalized patient is notified that the nursing rounds have started. In such circumstances, the predetermined first distance is set as appropriate in consideration of the number of the hospitalized patients to whom the nurse is assigned, and the time required for nursing rounds for each hospitalized patient, so that the hospitalized patient can be prevented from waiting for a long time after the hospitalized patient has been notified that the nursing rounds have started. Meanwhile, the predetermined first distance may be set to be longer in a case where the number of the hospitalized patients to whom the nurse is assigned is small, or the nursing rounds can be performed in a relatively short time by, for example, the nursing rounds being performed by a plurality of nurses.

The location management server 14 measures the distance between the nurse call slave device 1 and the nurse mobile phone 9 based on an actual distance over which the nurse moves to reach the location of the nurse call slave device 1, and sequentially selects the hospitalized patients. Therefore, in a case where a hospitalized patient associated with the nurse call slave device 1 is actually distant from the nurse mobile phone 9 by a distance longer than 20 meters since, for example, the nurse mobile phone 9 is on the upper floor or lower floor although the distance in the straight line therebetween is short, the hospitalized patient can be prevented from being selected.

When a hospitalized patient selected by the location management server 14 is not on the bed, the nursing-rounds start signal is transmitted to the hospitalized patient mobile phone 10 of the hospitalized patient. Therefore, in a case where the hospitalized patient who is carrying the hospitalized patient mobile phone 10 is outside the hospital room, the hospitalized patient can be notified that the nursing rounds have started even when the hospitalized patient is not in the hospital room. Thus, the hospitalized patient can prepare for the nursing rounds by, for example, returning to the hospital room.

In the nurse call system according to the present embodiment, in a case where, after the location management server 14 selects the hospitalized patients who are distant from the nurse mobile phone 9 by 20 meters or less, the distance between the nurse call slave device 1 of the selected hospitalized patient and the nurse mobile phone 9 becomes shorter such that the distance therebetween is less than or equal to 10 meters, the controller 8 is notified of the hospitalized patient who is distant from the nurse mobile phone 9 by 10 meters or less. The controller 8 performs control to further transmit the approach notification signal to the bedside monitor 3 of the hospitalized patient, and cause the bedside monitor 3 that has received the approach notification signal to make notification that the nurse will soon visit the hospital room. Therefore, the hospitalized patient can be notified that the nurse will soon visit the hospital room, and the hospitalized patient can further prepare for the nursing rounds without, for example, leaving the bed.

In the nurse call system according to the present embodiment, the controller 8 performs control to transmit the approach notification signal together with the location information of the nurse mobile phone 9 to the bedside monitor 3, and cause the bedside monitor 3 that has received the approach notification signal and the location information to make notification for the location of the nurse mobile phone 9. Therefore, the hospitalized patient can specifically know the present location of the nurse.

When the location management server has selected the hospitalized patients who are distant from the nurse mobile phone 9 by 10 meters, the controller 8 may determine whether or not the video analyzing unit detects the bed leaving state of each hospitalized patient.

In a case where the bed leaving state is not detected, the controller 8 performs control to transmit the approach notification signal to the bedside monitor 3 of the hospitalized patient. Meanwhile, in a case where the bed leaving state is detected, the controller 8 performs control to read the mobile phone information of the hospitalized patient from the patient-related information storage unit 71a, and transmit the approach notification signal to the hospitalized patient mobile phone 10 of the hospitalized patient.

The bedside monitor 3 or the hospitalized patient mobile phone 10 which has received the approach notification signal is controlled to display the present location of the nurse and make notification that the nurse will soon visit the hospitalized patient, as described above.

In such a configuration, in a case where the hospitalized patient is not on the bed, the approach notification signal is transmitted to the hospitalized patient mobile phone 10 of the hospitalized patient. Therefore, in a case where the hospitalized patient who is carrying the hospitalized patient mobile phone 10 is outside the hospital room, the hospitalized patient can be notified that the nurse will soon visit the hospital room. Thus, the hospitalized patient can prepare for the nursing rounds by, for example, quickly returning to the hospital room.

In the nurse call system according to the present embodiment, in a case where the distance between the nurse mobile phone 9 and the nurse call slave device 1 is less than or equal to 5 meters that is a preset distance, the controller 8 performs control to unlock the electronic key 4. Therefore, the electronic key 4 of the hospital room of the hospitalized patient to whom the nurse who performs the nursing rounds is assigned is automatically unlocked, so that the load and time, for the nurse, of unlocking the door of the hospital room can be eliminated, and the working efficiency of the nurse can be enhanced.

The distance, between the nurse mobile phone 9 and the nurse call slave device 1, at which the electronic key 4 is unlocked may be set to any distance. The electronic key 4 may be unlocked when the nursing-rounds start signal or the approach notification signal is transmitted.

In the nurse call system according to the present embodiment described above, the bedside monitor 3 is notified of the nursing-rounds start signal and the approach notification signal. However, the present invention is not limited to the embodiment. At least one of the nurse call slave device 1, the plate slave device 2, the bedside monitor 3, and the hospitalized patient mobile phone 10 may be notified of these signals.

In a case where the nursing-rounds start signal or the approach notification signal is transmitted to the nurse call slave device 1, the nurse call slave device 1 needs to have a notification control unit for performing control to make notification that the nursing rounds have started or that the nurse will soon visit the hospital room.

In the nurse call system according to the present embodiment, the approach notification signal is transmitted. However, the approach notification signal may not necessarily be transmitted. Furthermore, the electronic key 4 or the hospital room camera 5 may not necessarily be provided.

In the nurse call system according to the present embodiment, the controller 8 includes the patient-related information storage unit 71a. However, the nurse call master device 7 may include the patient-related information storage unit 71a or another storage device may have the patient-related information storage unit 71a.

In the nurse call system according to the present embodiment, the location management server 14 includes the nurse mobile phone location storage unit 81, the mobile phone/nurse association table 82, the nurse/hospitalized patient association table 83, the hospitalized patient/nurse call slave device association table 84, the bed location storage unit 85, and the map information storage unit 86. However, the controller 8, the nurse call master device 7, or another storage device may have any of them.

As described above, in the nurse call system according to the present invention, in a case where the nursing-rounds start operation is performed from the nurse mobile phone 9, the controller 8 performs control to cause the location management server 14 to sequentially select the hospitalized patients who satisfy the predetermined condition, based on the location information of the nurse mobile phone. Then, the controller 8 performs control to transmit the nursing-rounds start signal to at least one device among the bedside monitor 3, the nurse call slave device 1, the plate slave device 2, and the hospitalized patient mobile phone 10 of each of the hospitalized patients selected by the location management server 14, and cause the device that has received the nursing-rounds start signal to make notification that the nursing rounds have started. As long as the nurse call system has such a configuration, the other components may be configured in any manner.

A second embodiment of the present invention is described below.

A nurse call system according to the second embodiment of the present invention has the entire configuration that includes the nurse call slave device 1, the plate slave device 2, the bedside monitor 3, the electronic key 4, the hospital room camera 5, the corridor light 6, the nurse call master device 7, the controller 8, the nurse mobile phone 9, the hospitalized patient mobile phone 10, the IP-PBX 11, the nurse call server 13, the location management server 14, the common area camera 15, and the IMES transmitter 16, similarly to the nurse call system according to the first embodiment.

Figure 11:
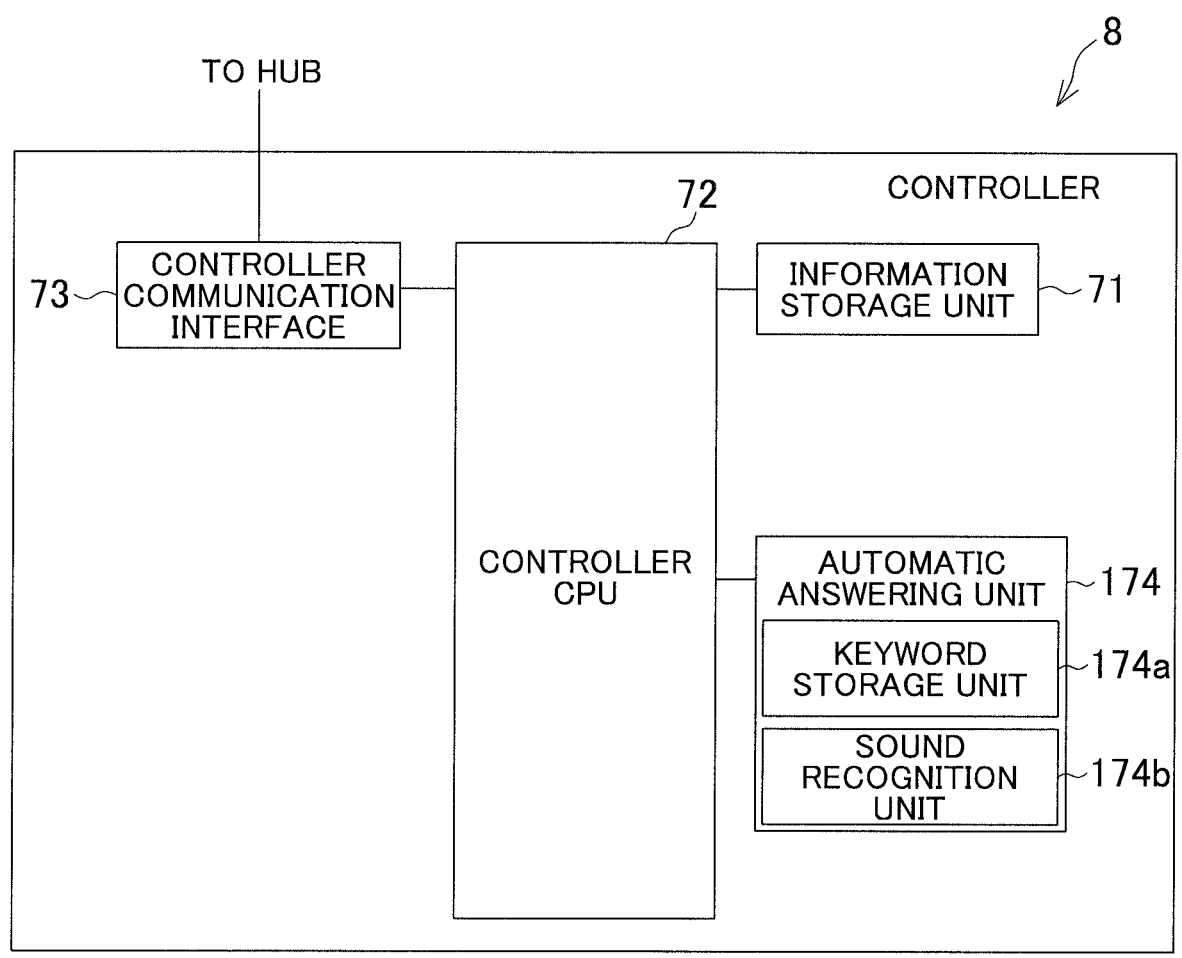
FIG. 11 is a functional block diagram illustrating a configuration of the controller 8 of a nurse call system according to a second embodiment of the present invention.

Meanwhile, the controller 8 of the present embodiment includes an automatic answering unit 174 in addition to the information storage unit 71 for storing various information, the controller CPU 72, and the controller communication IF 73, as shown in FIG. 11.

The automatic answering unit 174 includes a keyword storage unit 174a for storing a plurality of keyword groups, and a sound recognition unit 174b for recognizing a sound. Furthermore, the automatic answering unit 174 has a sound message for inquiring about a content required by a call.

The keyword storage unit 174a stores a first keyword group that includes keywords indicating that a call from the nurse call slave device 1 is a wrong call, and a second keyword group that includes keywords indicating that handling by the assigned nurse is required. The keyword storage unit 174a further stores a third keyword group that includes keywords indicating that highly urgent handling is not required (for example, a matter which can be handled relatively later), and a fourth keyword group that includes keywords indicating that handling by any nurse is required.

Such information is inputted as appropriate through operation on the nurse call master device 7.

As the first keyword group, words representing, for example, "wrong call", "inadvertently", and "merely pressed" are stored As the second keyword group, words representing, for example, "have a pain", "bad", "infusion", and "see me soon", are stored.

As the third keyword group, words representing, for example, "would like to talk with you", "water", "would like to drink", "please buy a television card for me", and "would like to go out" are stored.

As the fourth keyword group, words representing, for example, "posture", "orientation of the body", and "toilet" are stored.

The hospitalized patient mobile phone 10 can be set to be used as a part of the nurse call system, and, for example, can receive notification that the nurse will soon visit for nursing rounds.

The server CPU 87 of the location management server 14 controls update of the location information of the nurse mobile phone 9, controls selection of the nurse mobile phone to be called, and further controls the entire location management server 14.

The hospital room camera 5 of the present embodiment may not necessarily include the video analyzing unit capable of detecting the bed leaving state in which a hospitalized patient is not on the bed.

The operation of the nurse call system according to the present embodiment having the above-described configuration will be described below.

The sound notification operation of the nurse call master device 7 and the nurse mobile phone 9 that are called by the nurse call slave device 1, and the answering operation of the nurse call master device 7 or the nurse mobile phone 9 are the same as in conventional art. Therefore, the description of such operations is omitted, and an operation performed when the nurse is called will be described.

As described above, the location information of each nurse mobile phone 9 is regularly transmitted to the location management server 14, and the server CPU 87 performs control such that data in the nurse mobile phone location storage unit 81 is rewritten and saved with the latest data.

In a case where the hospitalized patient presses the call button 1a of the nurse call slave device 1 to make a call, the controller 8 causes the automatic answering unit 174 to automatically answer the call. At this time, the nurse call master device 7 and the nurse mobile phone 9 are not called.

Specifically, the automatic answering unit 174 answers the call from the nurse call slave device 1, and, thus, a communication line is established between the controller 8 and the bedside monitor 3 of the hospitalized patient who has made the call from the nurse call slave device 1, and a matter-required-by-call confirmation signal for confirming a matter required by the call is transmitted to the bedside monitor 3.

The bedside monitor 3 that has received the matter-required-by-call confirmation signal reproduces, through the loudspeaker 35, a sound message such as "How can I help you?" for confirming the matter required by the call, under the control of the side monitor CPU 37. In the present embodiment, the matter required by the call is confirmed by a sound message. However, the present invention is not limited to the embodiment, and, for example, a character message may be displayed on the monitor 31 together with the use of the sound message, or the matter may be confirmed merely by the display of a character message.

The hospitalized patient, who hears the sound message, speaks about the required matter through the microphone 34.

The sound data (content in the call) of the hospitalized patient is transmitted via the side monitor communication IF 38 to the controller 8 under the control of the side monitor CPU 37.

The automatic answering unit 174 of the controller 8 recognizes the sound data of the hospitalized patient through the sound recognition unit 174b, and confirms whether or not the sound data includes the predetermined keyword stored in the keyword storage unit 174a.

In a case where the sound data of the hospitalized patient includes the first keyword group indicating a wrong call, the controller 8 performs control to transmit, to the bedside monitor 3 of the hospitalized patient, a cancel confirmation signal for confirming whether or not the call from the nurse call slave device 1 is to be cancelled.

Figure 12:
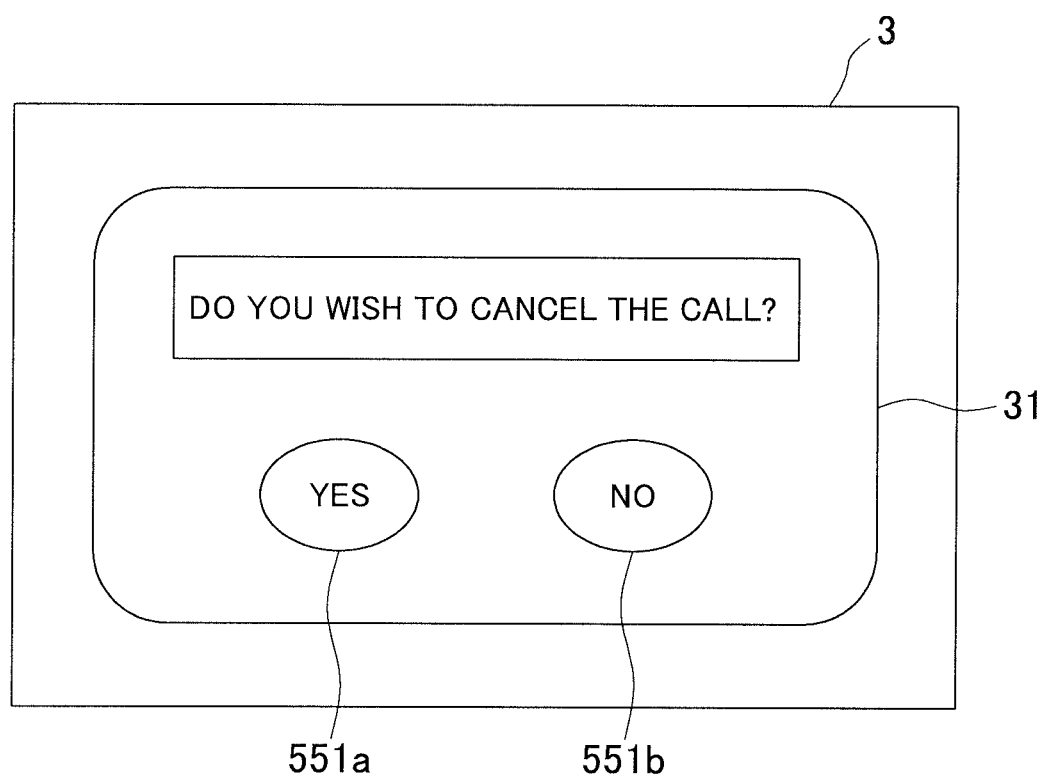
FIG. 12 illustrates an example of a display screen of the bedside monitor 3 of the nurse call system according to the second embodiment.

The bedside monitor 3 that has received the cancel confirmation signal reproduces a sound message such as "Do you wish to cancel the call?" and, as shown in FIG. 12, displays the character message together with selection buttons 551a and 551b representing "Yes" and "No", on the monitor 31, under the control of the side monitor CPU 37. In the present embodiment, whether or not the call is to be cancelled is confirmed by the character message and the sound message. However, the present invention is not limited to the embodiment, and, for example, the confirmation may be performed merely by reproducing the sound message, or merely by displaying the character message.

In a case where the hospitalized patient cancels the call, the hospitalized patient touches the selection button 551a representing "Yes" displayed on the monitor 31 of the bedside monitor 3.

In a case where a signal indicating that the hospitalized patient has touched the selection button 551a representing "Yes" is transmitted to the controller 8 via the side monitor communication IF 38 under the control of the side monitor CPU 37, the controller 8 performs control to cancel the call from the nurse call slave device 1, and end the communication between the controller 8 and the bedside monitor 3.

Meanwhile, in a case where the hospitalized patient does not cancel the call, the hospitalized patient touches the selection button 551b representing "No" displayed on the monitor 31 of the bedside monitor 3.

In a case where a signal indicating that the hospitalized patient has touched the selection button 551b representing "No" is transmitted to the controller 8 via the side monitor communication IF 38 under the control of the side monitor CPU 37, the controller 8 performs control to transmit again the matter-required-by-call confirmation signal to the bedside monitor 3, and confirms the matter required by the call through the bedside monitor 3 as described above. The sound data of the required matter as said by the hospitalized patient through the microphone 34 is transmitted to the controller 8 via the side monitor communication IF 38. The automatic answering unit 174 of the controller 8 causes the sound recognition unit 174b to recognize the sound data of the hospitalized patient, and confirms again whether or not the sound data includes the predetermined keyword stored in the keyword storage unit 174a.

In a case where the sound data of the hospitalized patient includes the first keyword group indicating a wrong call, the controller 8 performs the above-described control.

In a case where the sound data inputted by the hospitalized patient for the second time includes the first keyword group again, the assigned nurse or the like may be called. Furthermore, a nurse or the like may be called at a time when the selection button 551b representing "No" is touched.

In a case where the sound data of the hospitalized patient includes the second keyword group indicating that handling by the assigned nurse is required, the controller 8 performs the following control with reference to the mobile phone/nurse association table 82, the nurse/hospitalized patient association table 83, and the hospitalized patient/nurse call slave device association table 84 in the location management server 14. Specifically, the controller 8 performs control to specify a nurse associated with the hospitalized patient who has made the call from the nurse call slave device 1, specify the nurse mobile phone 9 associated with the nurse, call the specified nurse mobile phone 9, and end the communication between the controller 8 and the bedside monitor 3.

The controller 8 may perform control for both calling the specified nurse mobile phone 9 and calling the nurse call master device 7. In a case where the specified nurse mobile phone 9 does not answer the call, the controller 8 may perform control to call another nurse mobile phone 9, for example, the nurse mobile phone 9 near the location of the nurse call slave device 1 as described below.

Meanwhile, in a case where the sound data of the hospitalized patient includes the third keyword group indicating that highly urgent handling is not required, the controller 8 performs the following control with reference to the mobile phone/nurse association table 82, the nurse/hospitalized patient association table 83, and the hospitalized patient/nurse call slave device association table 84 in the location management server 14. Specifically, the controller 8 performs control to specify a nurse associated with the hospitalized patient who has made a call from the nurse call slave device 1, specify the nurse mobile phone 9 associated with the nurse, and transmit a message representing a matter required by the call from the hospitalized patient, such as "Ms./Mr. X in Room No. 303 would like to drink water", to the specified nurse mobile phone 9. At this time, the controller 8 does not perform control to call the nurse mobile phone 9 of the assigned nurse.

In a case where the sound data of the hospitalized patient includes the fourth keyword group indicating that handling by any nurse is required, the controller 8 performs the following control by using the nurse mobile phone location storage unit 81, the mobile phone/nurse association table 82, the hospitalized patient/nurse call slave device association table 84, the bed location storage unit 85, and the map information storage unit 86. Specifically, the controller 8 performs control to cause the location management server 14 to read a location of the nurse call slave device 1 (bed) that has made the call, select a nurse near the location of the nurse call slave device 1, and call the nurse mobile phone 9 of the nurse, and end the communication between the controller 8 and the bedside monitor 3.

The map information storage unit 86 measures the distance between the nurse call slave device 1 and the nurse mobile phone 9 based on the actual distance over which the nurse moves to reach the location of the nurse call slave device 1, to select the nurse near the location of the nurse call slave device 1.

The controller 8 may perform control to call the selected nurse mobile phone 9 near the location of the nurse call slave device 1 and also call the nurse call master device 7. In a case where the specified nurse mobile phone 9 does not answer the call, the controller 8 may perform control to call another nurse mobile phone 9.

In a case where the sound data of the hospitalized patient does not include any of the second keyword group to the fourth keyword group, the controller 8 performs control to call the nurse call master device 7.

The controller 8 may perform control to call the nurse mobile phone 9 of the assigned nurse or the nurse mobile phone 9 near the location of the nurse call slave device 1, or may perform control to call both the nurse mobile phone 9 described above and the nurse call master device 7.

The above description mentions the operation performed by the nurse call system when the hospitalized patient presses the call button 1a of the nurse call slave device 1 to make a call. In the case of a call, such as a staff call, a call for toilet, or a bath call, which requires a predetermined matter to be highly urgently handled by nursing work, the controller 8 performs control to call the nurse call master device 7 or the nurse mobile phone 9 without answering performed automatically by the automatic answering unit 174.

Thus, in the nurse call system according to the second embodiment, at least a part of the calls from the nurse call slave devices 1 is primarily answered automatically by the automatic answering unit 174 of the controller 8 without calling the nurse call master device 7 and the nurse mobile phone 9, thereby reducing load of nursing work caused by the insufficient number of nurses.

In a case where a call from the nurse call slave device 1 is a wrong call caused by, for example, an erroneous operation, the call from the nurse call slave device 1 can be canceled before the nurse call master device 7 or the nurse mobile phone 9 is called. Therefore, an unnecessary call can be eliminated to reduce load of the nursing work.

In the case of a call that requires handling by the assigned nurse, the assigned nurse is called. Meanwhile, in the case of a call that requires handling by any of nurses including the assigned nurse and other nurses, the nurse mobile phone of any of the nurses who is near the nurse call slave device that has made the call is called. Furthermore, in the case of the predetermined urgent call, the nurse call master device or the nurse mobile phone is immediately called without answering performed automatically by the automatic answering unit 174. The calling can be performed according to the content in the call.

In the nurse call system according to the present embodiment, in a case where the content in the call includes the fourth keyword group indicating that handling by any nurse is required, the controller 8 performs control to call the nurse mobile phone 9 of a nurse near the location of the nurse call slave device 1. However, in a case where the content in the call does not include any of the first keyword group to the third keyword group, the nurse mobile phone 9 of a nurse near the location of the nurse call slave device 1 may be called.

The nurse mobile phone 9 of a nurse, among all the nurses, who is near the location of the nurse call slave device 1 that has made a call may be called, or the nurse mobile phone 9 of a nurse, near the location of the nurse call slave device 1 that has made a call, among the nurses in a nurse group (including the assigned nurse) that is assigned to the hospitalized patient who has made the call, may be called. In the latter case, the nurse group that is assigned to the hospitalized patient needs to be registered in the nurse/hospitalized patient association table 83 in advance.

In the nurse call system according to the present embodiment, the matter-required-by-call confirmation signal and the cancel confirmation signal are transmitted to the bedside monitor 3. However, the present invention is not limited to the embodiment. These signals may be transmitted to the nurse call slave device 1 or the plate slave device 2. In a case where these signals are transmitted to the nurse call slave device 1, the nurse call slave device 1 needs to have a loudspeaker or a microphone.

In the nurse call system according to the present embodiment, the controller 8 has the automatic answering unit 174. However, the plate slave device 2 or the corridor light 6 may have the automatic answering unit 174 or another storage device may have the automatic answering unit 174.

In the nurse call system according to the present embodiment, the location management server 14 has the nurse mobile phone location storage unit 81, the mobile phone/nurse association table 82, the nurse/hospitalized patient association table 83, the hospitalized patient/nurse call slave device association table 84, the bed location storage unit 85, and the map information storage unit 86. However, the controller 8, the nurse call master device 7, or another storage device may have any of them.

As described above, in the nurse call system according to the present invention, the plate slave device 2, the corridor light 6, or the controller 8 has an automatic answering unit for automatically answering a call from the nurse call slave device 1, and at least a part of the calls from the nurse call slave devices 1 is controlled to be automatically answered by the automatic answering unit without calling the nurse call master device 7 and the nurse mobile phone 9. As long as the nurse call system has such a configuration, the other components may be configured in any manner.

A third embodiment of the present invention is described below.

A nurse call system according to the third embodiment of the present invention has the entire configuration that includes the nurse call slave device 1, the plate slave device 2, the bedside monitor 3, the electronic key 4, the hospital room camera 5, the corridor light 6, the nurse call master device 7, the controller 8, the nurse mobile phone 9, the hospitalized patient mobile phone 10, the IP-PBX 11, the nurse call server 13, the location management server 14, the common area camera 15, and the IMES transmitter 16, similarly to the nurse call system according to the first embodiment.

Figure 13:
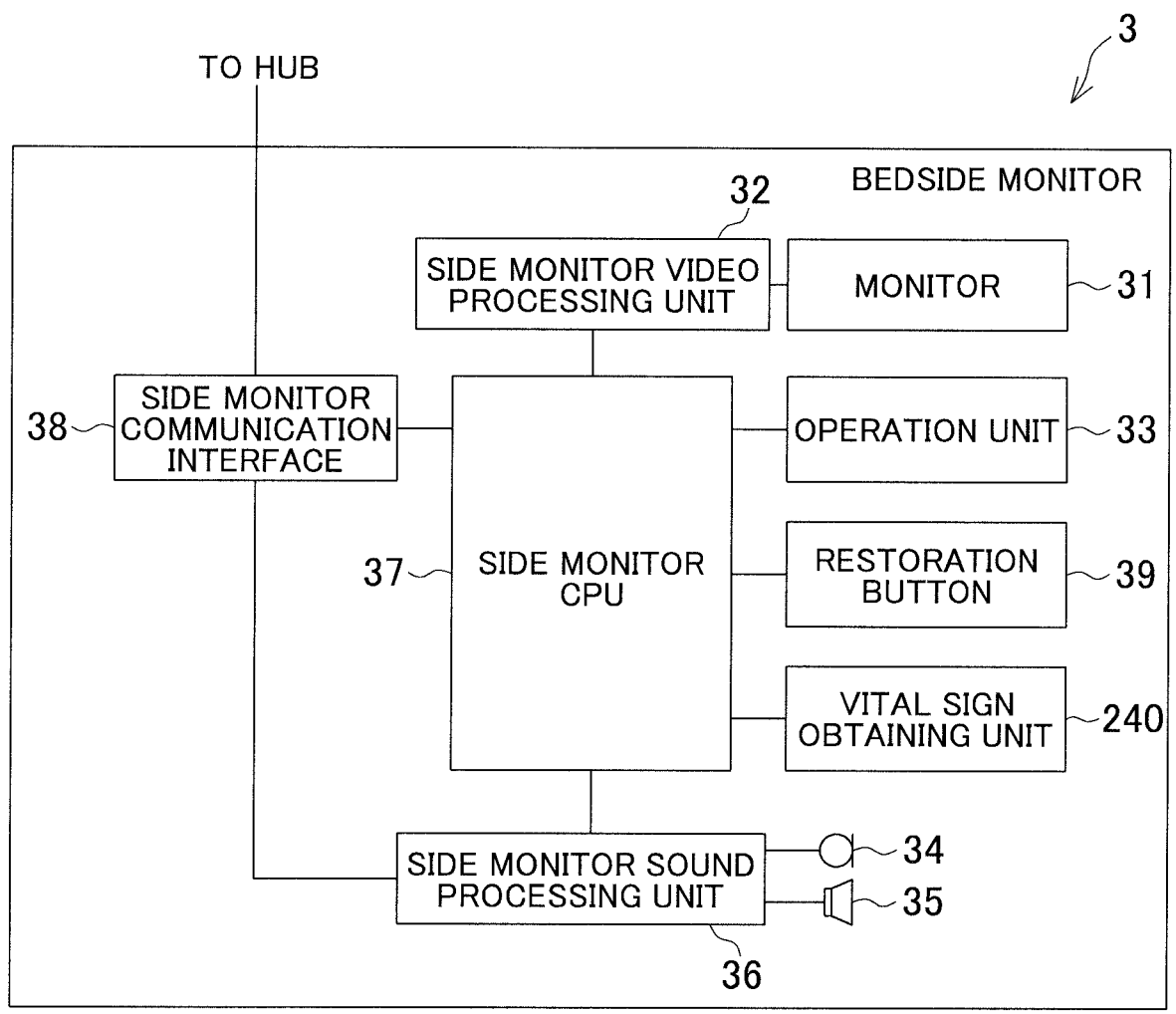
FIG. 13 is a functional block diagram illustrating a configuration of the bedside monitor 3 of a nurse call system according to a third embodiment of the present invention.

Meanwhile, the bedside monitor 3 of the present embodiment includes a vital sign obtaining unit 240, in addition to the monitor 31, the side monitor video processing unit 32, the operation unit 33, the microphone 34 and the loudspeaker 35, the side monitor sound processing unit 36, the side monitor CPU 37, the side monitor communication IF 38, and the restoration button 39, as shown in FIG. 13.

The vital sign obtaining unit 240, when enabled, can perform personal authentication and measure a vital sign such as a pulse, a blood pressure, or a body temperature by touching of a predetermined body portion of the hospitalized patient, for example, a finger pulp of an index finger.

The personal authentication is performed by, for example, determining whether or not vein information or fingerprint information of a finger pulp of an index finger of a person who has touched the vital sign obtaining unit 240 matches vein information or fingerprint information, registered in advance, of the finger pulp of the index finger of the hospitalized patient.

Figure 14:
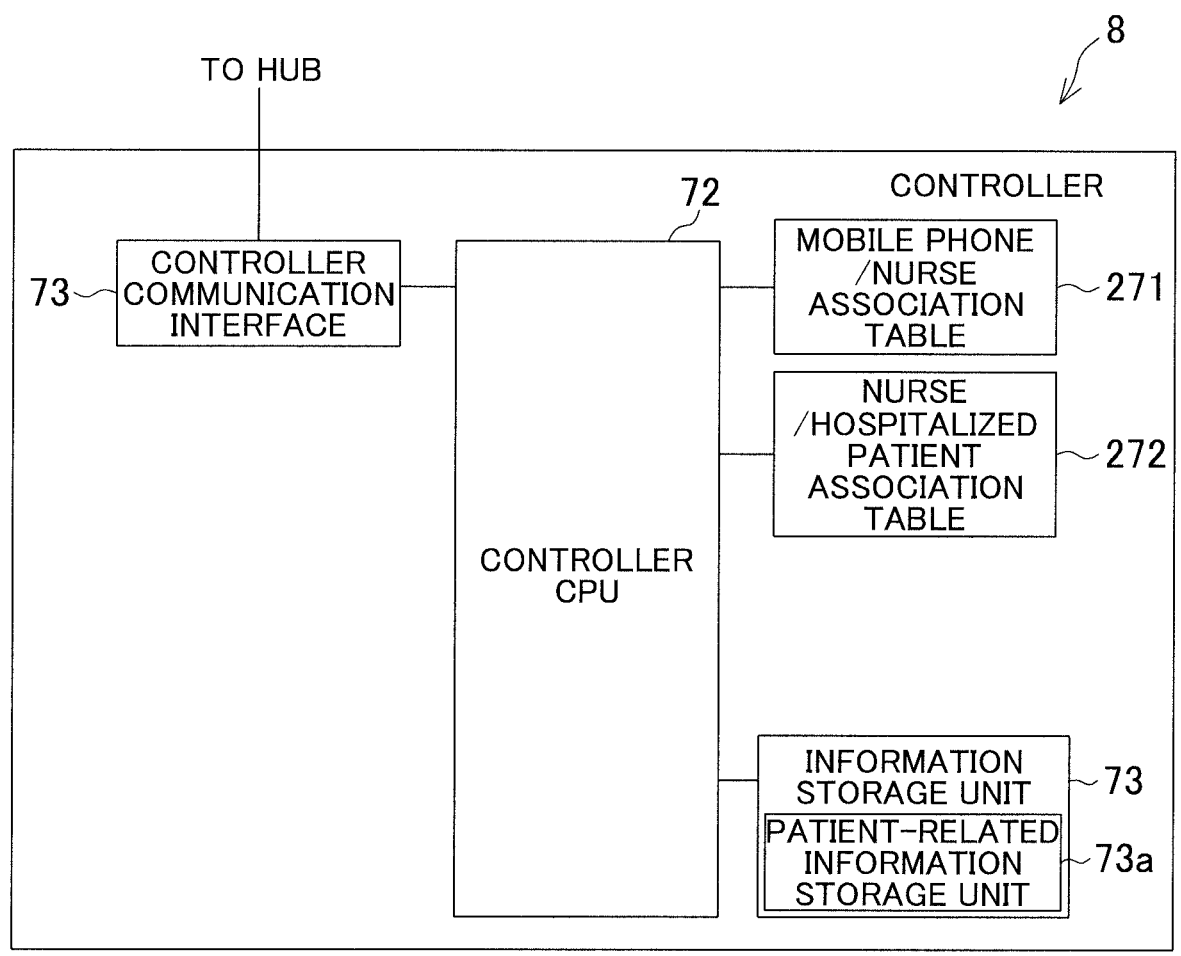
FIG. 14 is a functional block diagram illustrating a configuration of the controller 8 of a nurse call system according to the third embodiment and a fourth embodiment of the present invention.

The controller 8 of the present embodiment includes a mobile phone/nurse association table 271 in which a nurse and the nurse mobile phone 9 carried by the nurse are associated with each other, and a nurse/hospitalized patient association table 272 in which a nurse and a hospitalized patient are associated with each other, as shown in FIG. 14. The controller 8 further includes the information storage unit 71 for storing various information, the controller CPU 72 for controlling the controller 8, and the controller communication IF 73 for communicating with another device such as the corridor light 6, as shown in FIG. 14.

The information storage unit 71 includes the patient-related information storage unit 71a for storing the patient-related information. The patient-related information storage unit 71a stores patient information such as a name and an age of each hospitalized patient, vein information and fingerprint information of each hospitalized patient, nursing information such as a nursing classification and a medical specialty of each hospitalized patient, a slave device ID of the nurse call slave device 1, a bed number, schedule information about examinations, surgeries, and the like of each hospitalized patient, mobile phone information of the hospitalized patient mobile phone 10 of each hospitalized patient, and the like. Such information is inputted through operation on the nurse call master device 7.

In the present embodiment, the nurse mobile phone 9 can answer a call from the nurse call slave device 1, and can be set to transmit a vital sign measurement request signal.

The hospital room camera 5 of the present embodiment may not necessarily include the video analyzing unit capable of detecting a bed leaving state in which a hospitalized patient is not on the bed.

The operation of the nurse call system according to the present embodiment having the above-described configuration will be described below.

Calling for a nurse from the nurse call slave device 1, sound notification operations of the nurse call master device 7 and the nurse mobile phone 9 which are called, and an answering operation of the nurse call master device 7 or the nurse mobile phone 9 are the same as in conventional art. Therefore, the description of such operations is omitted, and an operation associated with measuring vital signs of hospitalized patients by themselves will be described.

In the present embodiment, the vital sign measurement request signal is set to be transmitted to the bedside monitor 3, and the vital sign obtaining unit 240 can measure the vital sign by the hospitalized patient touching the vital sign obtaining unit 240 with her/his finger.

The controller 8 transmits the vital sign measurement request signal to the bedside monitor 3 having the vital sign obtaining unit 240 at a predetermined preset time (for example, 8 a.m., 2 p.m., 8 p.m.) under the control of the controller CPU 72.

When the vital sign measurement request signal has been received, the bedside monitor 3 is controlled to enable the vital sign obtaining unit 240 for only a preset time period (for example, 5 minutes), and instruct the hospitalized patient to measure a vital sign, under the control of the side monitor CPU 37.

Figure 15:
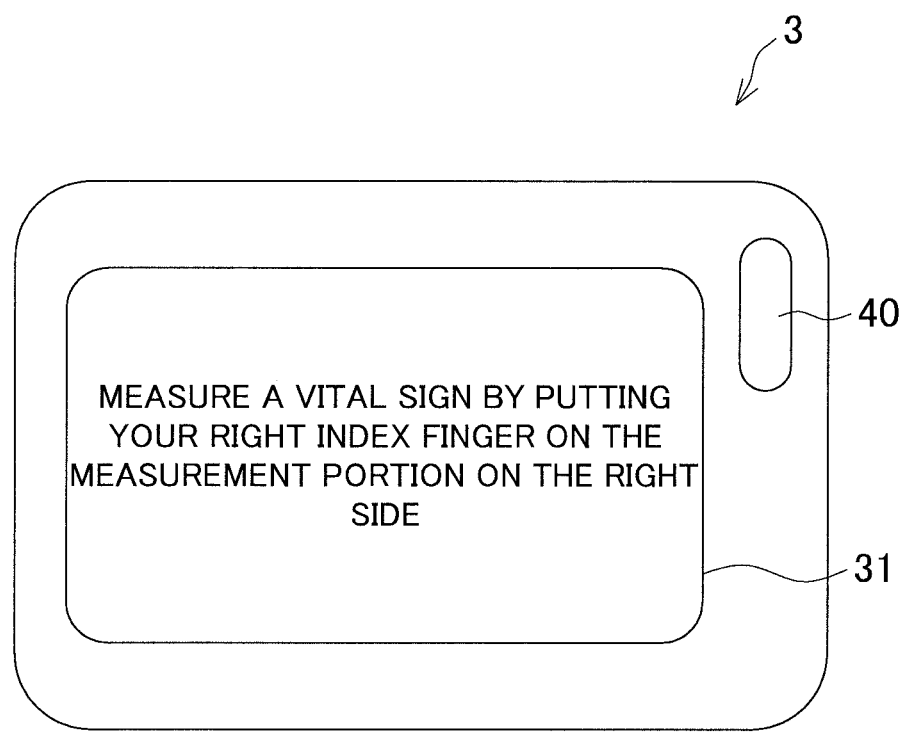
FIG. 15 illustrates a display screen of a monitor 31 of the bedside monitor 3 of the nurse call system according to the third embodiment.

Specifically, as shown in FIG. 15, a message indicating, for example, "Measure a vital sign by putting your right index finger on the measurement portion on the right side." is displayed on the monitor 31, and the notification is also made by sound from the loudspeaker 35. Such notification may be made only by display of the message or only by sound.

In response to such notification, the hospitalized patient touches, with the finger pulp of his/her index finger, the vital sign obtaining unit 240 of the bedside monitor 3 having been enabled.

With the hospitalized patient having touched the vital sign obtaining unit 240 with the finger pulp of his/her index finger, the side monitor CPU 37 reads the vein information or the fingerprint information of the finger pulp of his/her index finger that touches the vital sign obtaining unit 240. The controller 8 confirms whether or not the read vein information or fingerprint information of the finger pulp matches the vein information or the fingerprint information of the finger pulp of the hospitalized patient, which has been stored in the patient-related information storage unit 71a in advance, with reference to the patient-related information storage unit 71a in the controller 8, to perform personal authentication.

When the read information matches the stored information, the vital sign obtaining unit 240 measures a vital sign such as a pulse, a blood pressure, or a body temperature from the index finger that touches the vital sign obtaining unit 240.

Figure 16:
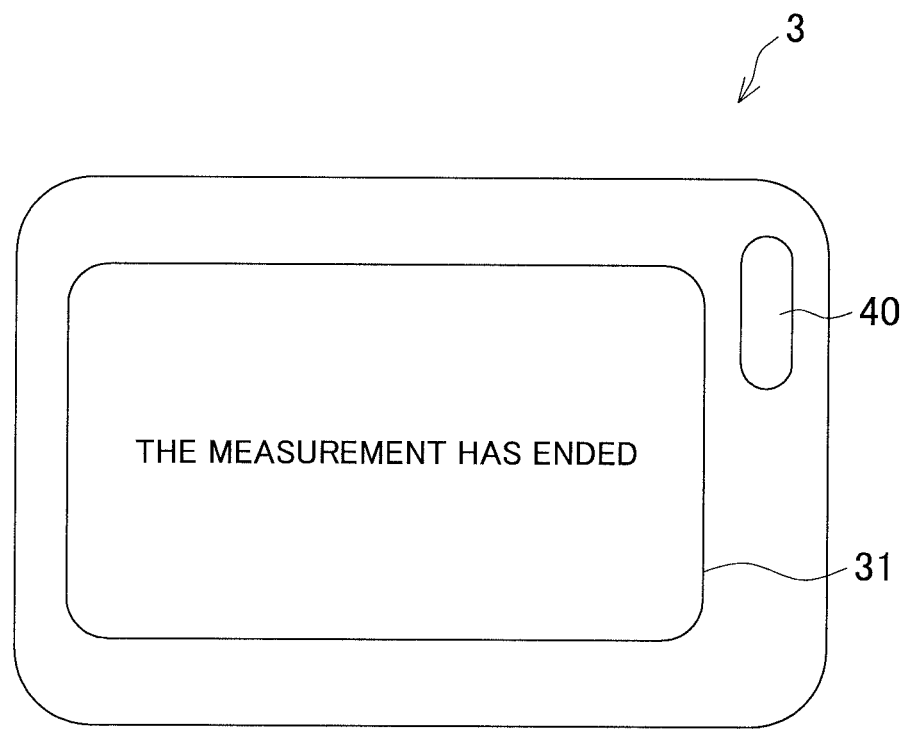
FIG. 16 illustrates a display screen of the monitor 31 of the bedside monitor 3 of the nurse call system according to the third embodiment.

When the measurement of the vital sign has ended, the vital sign obtaining unit 240 is controlled to be disabled, and to notify the hospitalized patient that the measurement of the vital sign has ended, under the control of the side monitor CPU 37. Specifically, as shown in FIG. 16, a message indicating, for example, "The measurement has ended." is displayed on the monitor 31, and the notification is also made by sound from the loudspeaker 35. Such notification may be made merely by display of the message or merely by sound, as described above.

When the measurement of the vital sign has ended, the bedside monitor 3 transmits, to the controller 8, the information of the measured vital sign together with predetermined patient information such as the name of the hospitalized patient, the slave device ID of the slave device 1, or the bed number, under the control of the side monitor CPU 37.

The controller 8 stores the received vital sign information in the patient-related information storage unit 71a or the like.

The assigned nurse is allowed to confirm the vital sign information stored in the patient-related information storage unit 71a or the like, and measure, as necessary, the vital sign of the hospitalized patient again, or nurse the hospitalized patient.

Thus, in the nurse call system according to the third embodiment, the vital sign of the hospitalized patient can be measured when the hospitalized patient touches the vital sign obtaining unit 240 with his/her predetermined body portion, and both the information of the measured vital sign and the predetermined patient information are transmitted to the controller 8. Therefore, the assigned nurse need not measure the vital sign of the hospitalized patient several times a day, thereby reducing load of the nursing work. When the vital sign is measured, the personal authentication is performed. Therefore, a person who measures the vital sign can be authenticated as the hospitalized patient him/herself, and the vital sign can then be measured.

In the nurse call system according to the present embodiment, the vital sign obtaining unit 240 is enabled at a predetermined preset time, and the hospitalized patient can be instructed to measure the vital sign, thereby requesting the hospitalized patient to regularly measure the vital sign.

Meanwhile, in a case where a result of the personal authentication indicates mismatching, the vital sign is not measured, so that the vital sign of another person can be prevented from being measured by mistake.

In a case where the vital sign information is not received from the bedside monitor 3 after elapse of a predetermined time (for example, 10 minutes) since transmission of the vital sign measurement request signal to the bedside monitor 3, the controller 8 performs control to transmit again the vital sign measurement request signal under the control of the controller CPU 72. When the vital sign measurement request signal has been received, the bedside monitor 3 enables again the vital sign obtaining unit 240 for a preset time period (for example, 5 minutes) and instructs the hospitalized patient to measure the vital sign, under the control of the side monitor CPU 37, as described above.

Thus, in the nurse call system according to the present embodiment, in a case where the vital sign cannot be measured in a state where, for example, the hospitalized patient is in the toilet or is temporarily outside the hospital room, the hospitalized patient can be instructed again to measure the vital sign.

When the vital sign information is not received from the bedside monitor 3 after elapse of a predetermined time since the vital sign measurement request signal has been transmitted again, the controller 8 performs control to transmit a non-receipt-of-vital-sign-information notification signal to the nurse mobile phone 9 of the nurse assigned to the hospitalized patient with reference to the mobile phone/nurse association table 271 and the nurse/hospitalized patient association table 272.

Thus, in the nurse call system according to the present embodiment, the assigned nurse can be notified that the vital sign has not been measured by the hospitalized patient in a predetermined time period after the vital sign measurement request signal has been transmitted again, so that the assigned nurse can perform handling as appropriate by, for example, visiting the hospital room of the hospitalized patient later.

The nurse call system allows the nurse mobile phone 9 of the assigned nurse to transmit the vital sign measurement request signal. Therefore, the vital sign measurement request signal can be transmitted from the nurse mobile phone 9 at a time, other than the predetermined timing which is preset in the controller 8, when the assigned nurse determines that the vital sign measurement request signal is to be transmitted. In the present embodiment, in a case where the vital sign information is not received from the bedside monitor 3 after elapse of a predetermined time since the vital sign measurement request signal has been transmitted again, the controller 8 performs control to transmit the non-receipt-of-vital-sign-information notification signal to the nurse mobile phone 9 of the nurse assigned to the hospitalized patient. However, the present invention is not limited to the embodiment. In a case where the vital sign information is not received from the bedside monitor 3 after elapse of a predetermined time since the vital sign measurement request signal has been transmitted to the bedside monitor 3, the controller 8 may perform the following control with reference to the mobile phone/nurse association table 271 and the nurse/hospitalized patient association table 272. Specifically, the controller 8 may perform control to transmit the vital sign measurement request signal again, and transmit the non-receipt-of-vital-sign-information notification signal to the nurse mobile phone 9 of the nurse assigned to the hospitalized patient. Alternatively, the controller 8 may perform control to transmit the non-receipt-of-vital-sign-information notification signal to the nurse mobile phone 9 of the nurse assigned to the hospitalized patient without transmitting the vital sign measurement request signal again.

In the present embodiment, the bedside monitor 3 has the vital sign obtaining unit 240. However, the present invention is not limited to the embodiment, and any of the nurse call slave device 1, the plate slave device 2, the bedside monitor 3, and the hospitalized patient mobile phone 10 may have the vital sign obtaining unit.

In the structure in which the hospitalized patient mobile phone 10 has the vital sign obtaining unit, predetermined application software needs to be installed.

Meanwhile, a vital sign communication unit capable of obtaining vital sign information from a wearable terminal (device for measuring the vital sign) that can measure the vital sign may be provided without providing the vital sign obtaining unit in one of the nurse call slave device 1, the plate slave device 2, the bedside monitor 3, and the hospitalized patient mobile phone 10.

The nurse call system having such a configuration can also obtain the vital sign information of the hospitalized patient.

In the present embodiment, the bedside monitor 3 has the vital sign obtaining unit 240, and the vital sign obtaining unit 240 performs the personal authentication and measures the vital sign. However, the personal authentication and measurement of the vital sign may be performed by the same device or different devices. For example, the nurse call system may be configured such that the nurse call slave device 1 has the vital sign obtaining unit and the plate slave device 2 performs the personal authentication.

For the personal authentication, not only the vein information and the fingerprint information of the hospitalized patient but also the slave device ID, the bed number, the telephone number of the hospitalized patient mobile phone 10, voice pattern information of the hospitalized patient, or the like may be used. The vital sign can be measured in any manner. Therefore, the vital sign may be measured not only by the finger pulp of the index finger touching the vital sign obtaining unit 240, but also by, for example, a predetermined body portion, of the hospitalized patient, such as the finger pulps of a plurality of fingers touching the vital sign obtaining unit 240.

In the nurse call system according to the present embodiment, the controller 8 has the patient-related information storage unit 71a for storing the vital sign information of the hospitalized patient. However, the nurse call master device 7 may have the patient-related information storage unit 71a or another storage device may have the patient-related information storage unit 71a.

In the nurse call system according to the present embodiment, the controller 8 has the mobile phone/nurse association table 271 and the nurse/hospitalized patient association table 272. However, the nurse call master device 7, the location management server 14, or another storage device may have one of the mobile phone/nurse association table 271 and the nurse/hospitalized patient association table 272.

As described above, in the nurse call system according to the present invention, one of the nurse call slave device 1, the plate slave device 2, the bedside monitor 3, and the hospitalized patient mobile phone 10 has the vital sign obtaining unit 240 or the vital sign communication unit capable of obtaining the vital sign information from a device for measuring the vital sign, and the vital sign information obtained through measurement by the vital sign obtaining unit 240 or the vital sign information obtained by the vital sign communication unit is controlled to be transmitted together with the predetermined patient information to the controller 8. As long as the nurse call system has such a configuration, the other components may be configured in any manner.

A fourth embodiment of the present invention is described below.

A nurse call system according to the fourth embodiment of the present invention has the entire configuration that includes the nurse call slave device 1, the plate slave device 2, the bedside monitor 3, the electronic key 4, the hospital room camera 5, the corridor light 6, the nurse call master device 7, the controller 8, the nurse mobile phone 9, the hospitalized patient mobile phone 10, the IP-PBX 11, the nurse call server 13, the location management server 14, the common area camera 15, and the IMES transmitter 16, similarly to the nurse call system according to the first embodiment.

Figure 17:
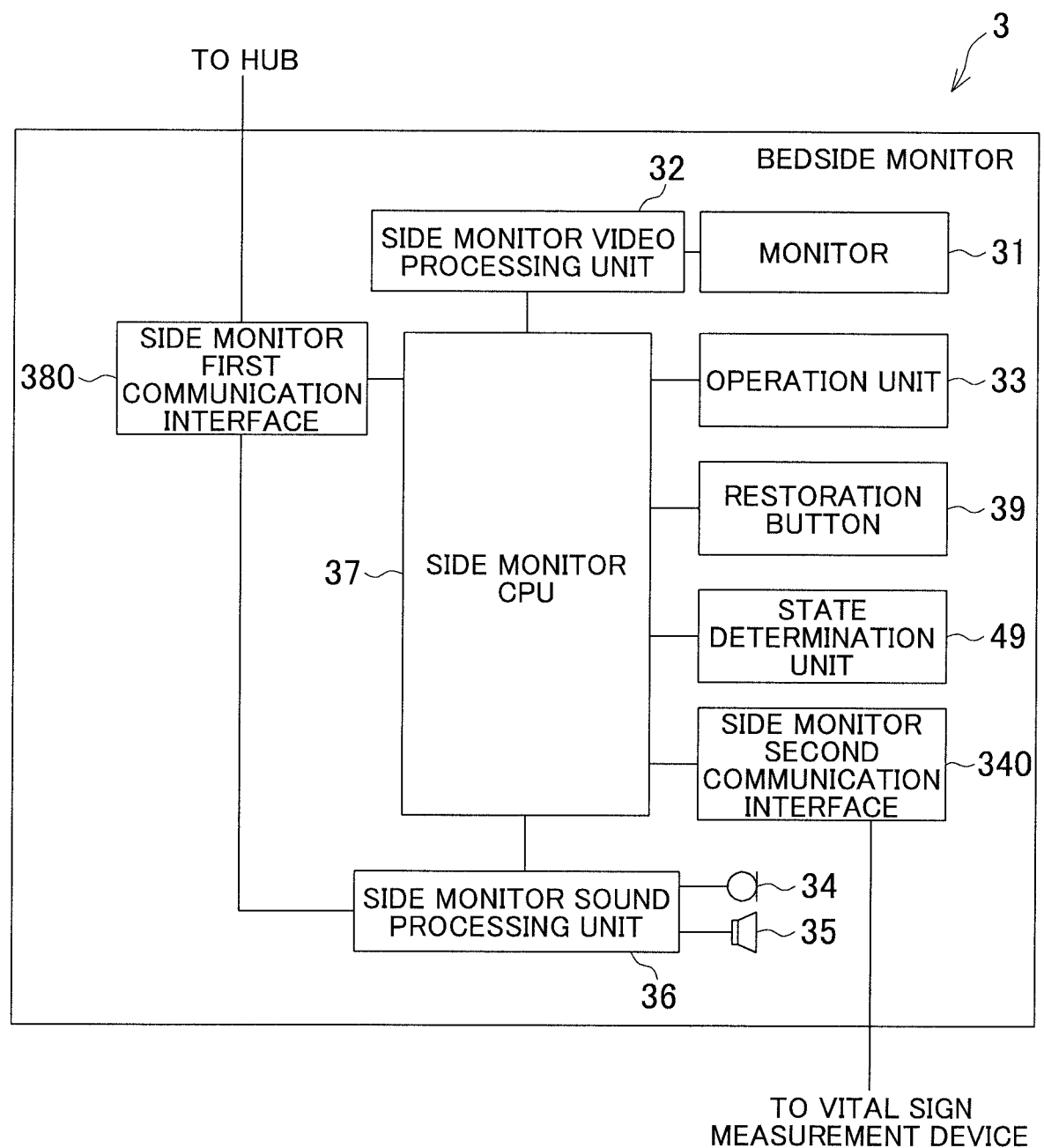
FIG. 17 is a functional block diagram illustrating a configuration of the bedside monitor 3 of the nurse call system according to the fourth embodiment.

Meanwhile, the bedside monitor 3 of the present embodiment is connected to a vital sign measurement device (not shown) for obtaining the vital sign information of the hospitalized patient through measurement. Furthermore, the bedside monitor 3 includes a side monitor second communication IF 340 and a state determination unit 49, in addition to the monitor 31, the side monitor video processing unit 32, the operation unit 33, the microphone 34 and the loudspeaker 35, the side monitor sound processing unit 36, the side monitor CPU 37, a side monitor first communication IF 380, and the restoration button 39, as shown in FIG. 17. The side monitor second communication IF 340 communicates with the vital sign measurement device. The state determination unit 49 determines whether or not a time at which the watching start signal has been received from the controller 8 is in a predetermined preset time range and determines whether or not the hospitalized patient is asleep based on the vital sign information obtained from the vital sign measurement device.

In the present embodiment, a time range (for example, from 10 p.m. to 7 a.m.) from lights out to the morning is set as the predetermined time range in the state determination unit 49.

The controller 8 of the present embodiment has the mobile phone/nurse association table 271, the nurse/hospitalized patient association table 272, the information storage unit 71, the controller CPU 72, and the controller communication IF 73, similarly to the controller 8 of the third embodiment shown in FIG. 14.

The information storage unit 71 includes the patient-related information storage unit 71a for storing the patient-related information.

The patient-related information storage unit 71a of the present embodiment stores patient information such as a name and an age of each hospitalized patient, nursing information such as a nursing classification, a medical specialty, and a doctor in charge of each hospitalized patient, a slave device ID of the nurse call slave device 1, a plate slave device ID, a bedside monitor ID, a bed number, a hospital room camera ID, schedule information about examinations, surgeries, and the like of each hospitalized patient, mobile phone information of the hospitalized patient mobile phone 10 of each hospitalized patient, and the like. Such information is inputted through operation on the nurse call master device 7.

Figure 18:
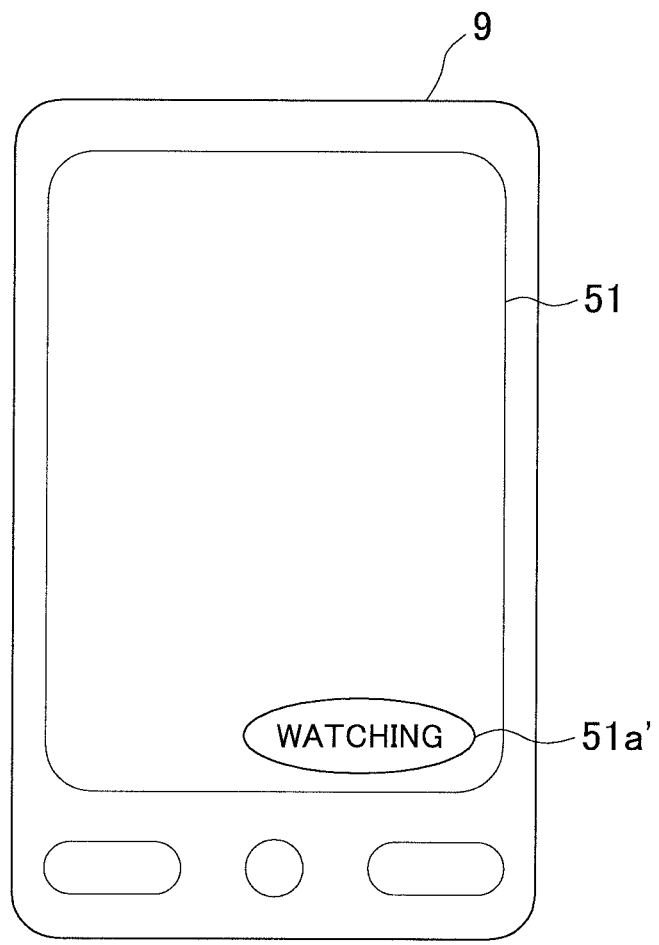
FIG. 18 illustrates a display screen of the nurse mobile phone 9 of the nurse call system according to the fourth embodiment.

The nurse mobile phone 9 of the present embodiment includes the display unit 51 that is implemented by a touch panel as shown in FIG. 18. The watching start button 51a' for starting the watching by a nurse is displayed on the display unit 51 by a predetermined operation performed by the nurse.

The hospital room camera 5 of the present embodiment may not necessarily include the video analyzing unit capable of detecting a bed leaving state in which a hospitalized patient is not on the bed.

The operation of the nurse call system having the above-described configuration will be described below.

Calling for a nurse from the nurse call slave device 1, sound notification operations of the nurse call master device 7 and the nurse mobile phone 9 which are called, and an answering operation of the nurse call master device 7 or the nurse mobile phone 9 are the same as in conventional art. Therefore, the description of such operations is omitted, and an operation performed when a nurse performs the watching start operation from the nurse mobile phone 9 will be described.

In the present embodiment, the vital sign measurement device constantly obtains the vital sign information of the hospitalized patient through measurement.

A nurse who intends to start the watching touches the watching start button 51a' of the nurse mobile phone 9. Thus, the controller 8 performs control to specify a hospitalized patient for whom the watching is to be performed and the bedside monitor 3 of the hospitalized patient with reference to the mobile phone/nurse association table 271, the nurse/hospitalized patient association table 272, and the patient-related information storage unit 71a. Then, the controller 8 performs control to transmit a watching start signal indicating that the watching starts, to the bedside monitor 3 of the hospitalized patient for whom the watching is to be performed.

In a case where the number of hospitalized patients for whom the watching is to be performed is plural, the watching start signal is transmitted to the bedside monitor 3 of one of the hospitalized patients selected by the controller 8 in the present embodiment. However, alternatively, the nurse call system may be configured such that the plurality of the hospitalized patients for whom the watching is to be performed are displayed on the nurse mobile phone 9 under the control of the controller 8, and the nurse selects hospitalized patients for whom the watching is to be performed through the nurse mobile phone 9. In this case, the watching start signal is transmitted to the bedside monitors 3 of the hospitalized patients selected through the nurse mobile phone 9.

At a time when the watching start signal has been received, the bedside monitor 3 determines whether or not the time is in a predetermined time range that is preset by the state determination unit 49, under the control of the side monitor CPU 37.

In a case where the time is not in the predetermined time range, the state determination unit 49 determines whether or not the hospitalized patient is asleep, based on the vital sign information obtained through measurement by the vital sign measurement device.

Figure 19:
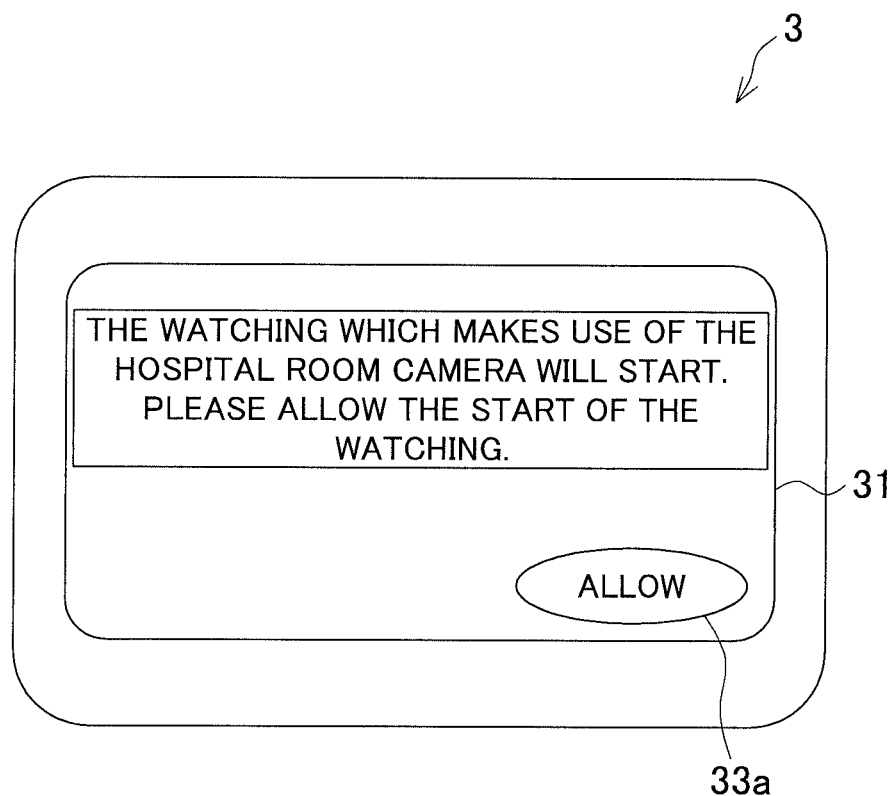
FIG. 19 illustrates a display screen of the monitor 31 of the bedside monitor 3 of the nurse call system according to the fourth embodiment.

In a case where the state determination unit 49 determines that the hospitalized patient is not asleep, a message, such as "The watching which makes use of the hospital room camera will start. Please allow the start of the watching." is displayed on the monitor 31 as shown in FIG. 19 for prompting the start-up of the hospital room camera 5 for the start of the watching to be allowed, and a sound message having the same content is outputted from the loudspeaker 35, under the control of the side monitor CPU 37. A timer (not shown) is started up and an allowing button 33*a* for allowing start-up of the hospital room camera 5 is displayed on the operation unit 33 under the control of the side monitor CPU 37.

The notification for prompting the start-up of the hospital room camera 5 for the start of the watching to be allowed may be displayed as a message on the monitor 31 and also outputted as a notification sound, or may be outputted merely as a sound message.

In a case where the hospitalized patient touches the allowing button 33*a* in a predetermined preset time period, a camera start-up allowing signal is transmitted from the bedside monitor 3 to the controller 8 under the control of the side monitor CPU 37.

When receiving the camera start-up allowing signal, the controller 8 performs control to specify the hospital room camera 5 associated with the hospitalized patient for whom the watching is to be performed, with reference to the patient-related information storage unit 71*a*. Then, the controller 8 performs control to start up the specified hospital room camera 5, and transmit the image taken by the hospital room camera 5 together with predetermined hospitalized patient information (for example, the name, the room number, the bed number, the nursing information, and the doctor in charge of the hospitalized patient) to the nurse mobile phone 9 on which the watching start operation has been performed.

Figure 20:
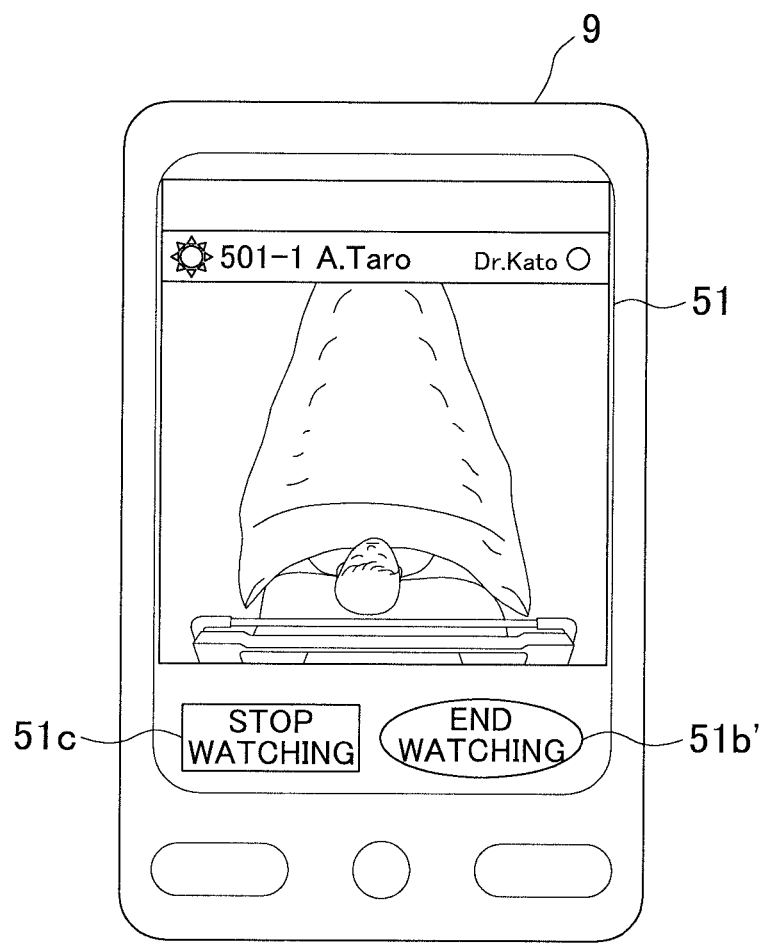
FIG. 20 illustrates a display screen of the nurse mobile phone 9 of the nurse call system according to the fourth embodiment.

Thus, as shown in FIG. 20, both the image taken by the hospital room camera 5 and the predetermined hospitalized patient information are displayed on the display unit 51 of the nurse mobile phone 9 on which the watching start operation has been performed.

In the nurse call system according to the fourth embodiment having such a configuration, a nurse is allowed to confirm the image taken by the hospital room camera 5 on the nurse mobile phone 9, to confirm the state of the hospitalized patient. Therefore, the necessary number of times the assigned nurse visits the hospital room of the hospitalized patient in one day in order to confirm the state of the hospitalized patient can be reduced, thereby reducing load of the nursing work.

In a case where the allowing button 33*a* is displayed on the operation unit 33, when the hospitalized patient has performed an operation for allowing the watching, the hospital room camera 5 is started up, thereby enhancing the privacy of the hospitalized patient.

In a case where the hospital room camera 5 is started up by the watching start operation, the controller 8 performs control to establish communication between the nurse mobile phone 9 on which the watching start operation has been performed and the bedside monitor 3 of the hospitalized patient.

In the nurse call system having such a configuration, a nurse can talk with the hospitalized patient while confirming the state of the hospitalized patient through the nurse mobile phone 9, so that the nurse can confirm the physical condition and the like, and can more correctly recognize the state of the hospitalized patient.

In a case where the nurse has confirmed the state of the hospitalized patient through the nurse mobile phone 9, the nurse touches the watching end button 51*b*', shown in FIG. 20, on the display unit 51 of the nurse mobile phone 9.

When the watching end button 51*b*' has been touched, the controller 8 performs control to stop the hospital room camera 5 associated with the hospitalized patient, and end the communication established between the nurse mobile phone 9 on which the watching start operation has been performed, and the bedside monitor 3 of the hospitalized patient.

In a case where another hospitalized patient for whom the watching is to be performed is present, the watching start signal is transmitted to the bedside monitor 3 of the hospitalized patient for whom the watching has not been performed yet.

In a case where a hospitalized patient for whom the watching is to be performed is not present, the watching ends.

Meanwhile, in a case where a hospitalized patient does not touch the allowing button 33*a* within the preset time period, the controller 8 performs control to stop the watching for the hospitalized patient without staring up the hospital room camera 5. In a case where the watching is to be performed for the other hospitalized patients, the watching start signal is transmitted to the bedside monitor 3 of the hospitalized patient for whom the watching has not been performed yet.

In a case where a hospitalized patient does not touch the allowing button 33*a*, the controller 8 may perform control to transmit the watching start signal to the bedside monitor 3 of the hospitalized patient after the watching for the other hospitalized patients has ended, or may perform control to display the hospitalized patient information of hospitalized patients for which the watching has not been performed, on the display unit 51 of the nurse mobile phone 9.

In a case where the state determination unit 49 determines that the hospitalized patient is asleep, the camera start-up allowing signal is transmitted from the bedside monitor 3 to the controller 8 under the control of the side monitor CPU 37, and the controller 8 performs control to start up the hospital room camera 5 without the watching allowing operation by the hospitalized patient, to start the watching as described above.

In the nurse call system having such a configuration, the watching can be smoothly performed in a case where the hospitalized patient is asleep.

Also in a case where the state determination unit 49 determines that the present time is in the predetermined preset time range, the camera start-up allowing signal is transmitted from the bedside monitor 3 to the controller 8 under the control of the side monitor CPU 37. Then, the controller 8 performs control to start up the hospital room camera 5 without the watching allowing operation by the hospitalized patient, to start the watching as described above.

In the nurse call system having such a configuration, the watching can be smoothly performed in a time range in which most of the hospitalized patients are assumed to be asleep.

In a case where a nurse needs to stop the watching halfway depending on the circumstances, the nurse touches a watching stop button 51*c* on the display unit 51 of the nurse mobile phone 9 as shown in FIG. 20.

By touching the watching stop button 51*c*, in a case where the hospital room camera 5 is in operation, the controller 8 performs control to stop the hospital room camera 5 and end the communication established between the nurse mobile phone 9 and the bedside monitor 3 of the hospitalized patient. Even in a case where another hospitalized patient for whom the watching is to be performed is present, the watching start signal is not transmitted to the bedside monitor 3 of the hospitalized patient for whom the watching has not been performed yet.

Figure 21:
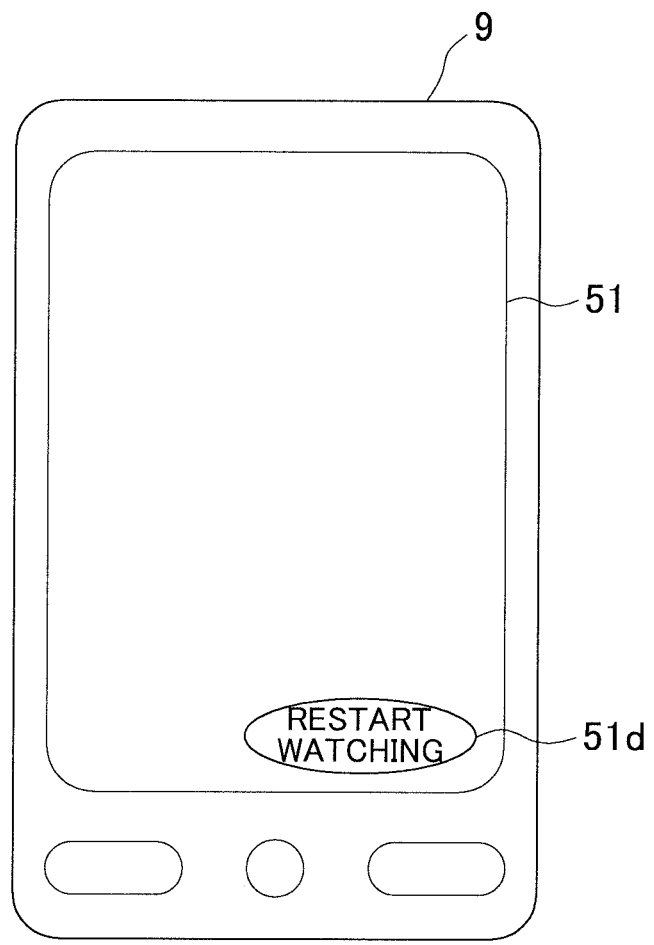
FIG. 21 illustrates a display screen of the nurse mobile phone 9 of the nurse call system according to the fourth embodiment.

By touching the watching stop button 51*c*, a watching restart button 51*d* is displayed on the display unit 51 of the nurse mobile phone 9 as shown in FIG. 21.

The nurse is allowed to restart the watching by touching the watching restart button 51*d*. Specifically, by touching the watching restart button 51*d*, the controller 8 performs control to transmit the watching start signal to the bedside monitor 3 of the hospitalized patient for whom the watching has not been performed yet.

In the nurse call system according to the present embodiment described above, the watching is started from the nurse mobile phone 9. However, the watching may be started from at least one of the nurse mobile phone 9 and the nurse call master device 7 which have watching start units such as the watching start buttons.

In the nurse call system according to the present embodiment, the bedside monitor 3 includes a watching allowing unit for allowing the start-up of the hospital room camera 5 according to the watching start operation. However, not the bedside monitor 3 but the hospital room camera 5, the nurse call slave device 1, or the plate slave device 2 of the hospitalized patient may include the watching allowing unit. In the nurse call system according to the present embodiment, the watching allowing unit is implemented by the allowing button 33*a* displayed on the operation unit 33. However, the watching may be allowed by using sound.

Meanwhile, such watching allowing unit may not necessarily be provided. In a case where the watching start operation has been performed from the nurse mobile phone 9 or the nurse call master device 7, before the hospital room camera 5 is started up to start taking an image, the controller 8 may cause any one of the hospital room camera 5, the nurse call slave device 1, the plate slave device 2, and the bedside monitor 3 to notify the hospitalized patient that the watching starts.

The notification that the watching starts may be made by a notification sound such as a knocking sound or by a sound message such as "A nurse will start the watching. The hospital room camera will start operating". A message may be displayed on the monitor 31 together with the notification sound or the sound message, or the notification may be made merely by a character message.

Thus, in a case where the nurse call system is configured such that, before the hospital room camera 5 is started up to start taking an image, the controller 8 performs control to cause any one of the hospital room camera 5, the nurse call slave device 1, the plate slave device 2, and the bedside monitor 3 to notify the hospitalized patient that the watching starts, the hospitalized patient can be notified that the watching using the hospital room camera 5 starts. Therefore, the privacy of the hospitalized patient can be enhanced.

Meanwhile, in response to the watching start operation from either the nurse mobile phone 9 or the nurse call master device 7 which includes the watching start unit such as the watching start button, the controller 8 may perform control to start up the hospital room camera 5 associated with a hospitalized patient who is registered as a hospitalized patient for whom the watching is to be performed, without making notification to the hospitalized patient.

In the nurse call system according to the present embodiment, in a case where the hospital room camera 5 is started up according to the watching start operation, the controller 8 performs control to establish communication between the nurse mobile phone 9 on which the watching start operation has been performed and the bedside monitor 3 of the hospitalized patient. However, communication between the nurse mobile phone 9 and the hospital room camera 5, the nurse call slave device 1, or the plate slave device 2 of the hospitalized patient instead of the bedside monitor 3 may be established. In a case where the communication between the nurse mobile phone 9 and the nurse call slave device 1 is established, the nurse call slave device 1 needs to have a microphone and a loudspeaker. The same applies to a case where communication between the nurse mobile phone 9 and the hospital room camera 5 is established.

Meanwhile, in a case where the hospital room camera 5 is started up according to the watching start operation, communication between the nurse mobile phone 9 on which the watching start operation has been performed and any one of these devices may not necessarily be established.

In the nurse call system according to the present embodiment, the bedside monitor 3 is connected to the vital sign measurement device for obtaining the vital sign information of the hospitalized patient through measurement. The controller 8 causes the state determination unit 49 to determine whether or not a time at which the watching start signal has been received from the controller 8 is in the predetermined time range or whether or not the hospitalized patient is asleep when the watching start signal has been received. However, the controller 8 may determine whether or not the time is in the predetermined time range.

The state determination unit 49 may not necessarily be provided. Specifically, the nurse call system may be structured such that the vital sign measurement device is not provided and the vital sign of the hospitalized patient is not measured. In other words, the nurse call system may be structured such that the bedside monitor 3 is not connected to the vital sign measurement device and the state determination unit 49 does not determine whether or not the hospitalized patient is asleep, or does not determine whether or not the present time at which the watching start signal is received from the controller 8 is in the predetermined preset time range.

In the nurse call system according to the present embodiment, the controller 8 includes the mobile phone/nurse association table 271 and the nurse/hospitalized patient association table 272. However, the nurse call master device 7, the location management server 14, or another storage device may have any one of them.

As described above, in the nurse call system according to the present invention, the controller 8 performs control to start up the hospital room camera 5 associated with a hospitalized patient registered as a hospitalized patient for whom the watching is to be performed, in response to the watching start operation from either the nurse mobile phone 9 or the nurse call master device 7 that has the watching start unit such as the watching start button, and transmit the image taken by the hospital room camera 5 to the nurse mobile phone 9 or the nurse call master device 7 on which the watching start operation has been performed. As long as the nurse call system has such a configuration, the other components may be configured in any manner. The nurse call system may not necessarily have the location specifying system, the electronic key 4, and/or the hospitalized patient mobile phone 10.

A fifth embodiment of the present invention is described below.

Figure 22:
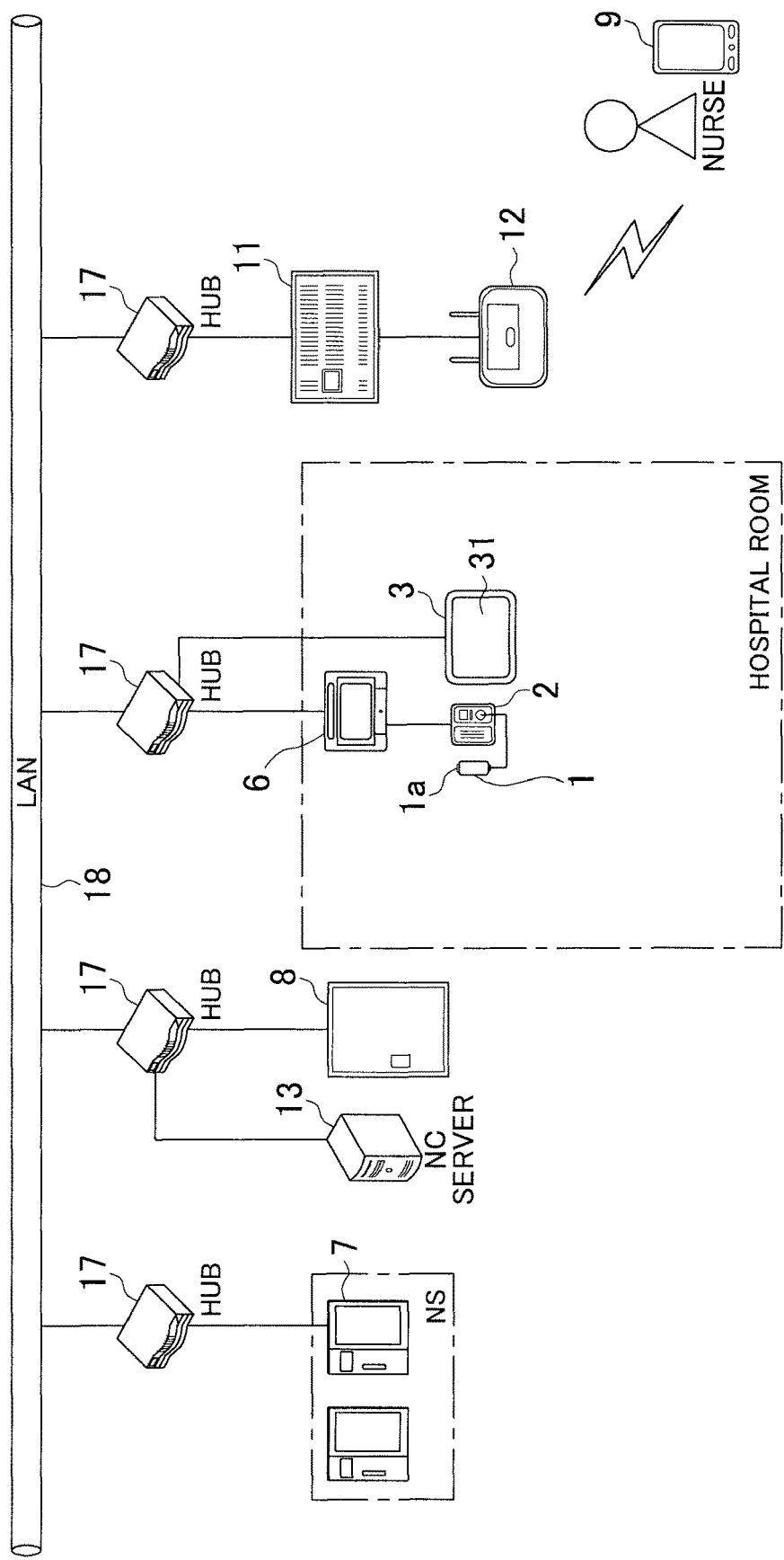
FIG. 22 illustrates the entire configuration of a nurse call system according to a fifth embodiment of the present invention.

FIG. 22 illustrates a configuration of a nurse call system according to the fifth embodiment of the present invention. As shown in FIG. 22, the nurse call system according to the present embodiment includes the nurse call slave device 1 provided for each bed in a hospital room for allowing a hospitalized patient to call a nurse, the plate slave device 2 to which the nurse call slave device 1 is connected and which is provided on a wall surface near the bed in the hospital room, and the bedside monitor 3 that is provided for each bed in the hospital room and is capable of displaying patient-related information. The nurse call system further includes the corridor light 6 provided on a corridor wall surface near the hospital room for making notification that a call is occurring, the nurse call master device 7 provided at a nurse station for answering a call from the nurse call slave device 1, the controller 8 for controlling the devices such as the nurse call slave device 1, the corridor light 6, and the nurse call master device 7, and the nurse mobile phone 9 carried by a nurse.

Furthermore, the nurse call system includes the IP-PBX 11 which is connected to the controller 8, the base station 12 that allows communication between the nurse mobile phone 9 and the IP-PBX 11, and the nurse call server 13 for storing various data about the hospitalized patient.

The plate slave device 2, to which the nurse call slave device 1 is connected, is connected to the corridor light 6 via a transmission line. The bedside monitor 3, the nurse call master device 7, the controller 8, the corridor light 6, the IP-PBX 11, the nurse call server 13, the location management server 14, and the common area camera 15 are connected via the HUBs 17 to the LAN 18 provided in the hospital.

The IP-PBX 11 is connected to the base station 12 via the transmission line. The base stations 12 are set at a plurality of locations in the facilities as appropriate.

The nurse call slave device 1 has a call button for calling a nurse, and is connected to the plate slave device 2.

FIG. 3 is a functional block diagram illustrating the plate slave device 2. As shown in FIG. 3, the plate slave device 2 includes the nurse call slave device connection unit 21 for making connection to the nurse call slave device 1, the microphone 22 and the loudspeaker 23 for speaking, and the slave device sound processing unit 24 for processing a sound signal. The plate slave device 2 further includes the slave device CPU 25 for controlling the plate slave device 2, the slave device communication IF 26 for communicating with the corridor light 6, and the restoration button 27 capable of stopping a calling operation and the like.

FIG. 4 is a functional block diagram illustrating the bedside monitor 3. As shown in FIG. 4, the bedside monitor 3 includes the monitor 31 that is implemented by an LCD for displaying various information, the side monitor video processing unit 32 for processing video images to be displayed on the monitor 31, the operation unit 33 that is implemented by a touch panel for performing various operations, the microphone 34 and the loudspeaker 35 for speaking, and the side monitor sound processing unit 36 for processing a sound signal. The bedside monitor 3 further includes the side monitor CPU 37 for controlling the bedside monitor 3, the side monitor communication IF 38 for communicating with the controller 8, and the restoration button 39 capable of performing operation such as stopping a notification operation and the like, and turning on/off the liquid crystal display.

Figure 23:
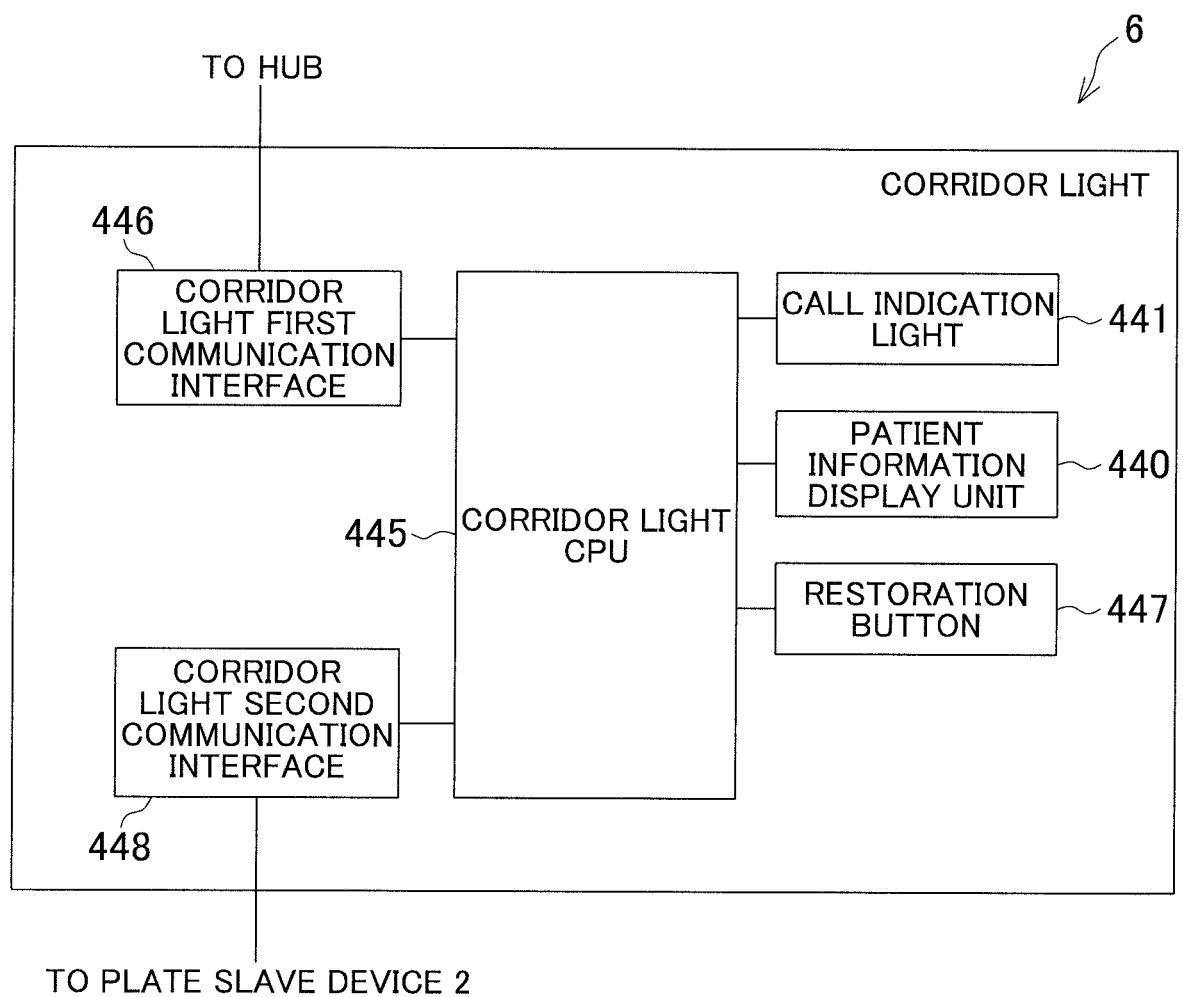
FIG. 23 is a functional block diagram illustrating a configuration of the corridor light 6 of the nurse call system according to the fifth embodiment.

FIG. 23 is a functional block diagram illustrating the corridor light 6. As shown in FIG. 23, the corridor light 6 includes a patient information display unit 440 for displaying patient information such as a name of a patient in the hospital room, a call indication light 441 for indicating occurrence of a call from a hospitalized patient by light emission, and a corridor light CPU 445 for controlling the corridor light 6. The corridor light 6 further includes a corridor light first communication IF 446 for communicating with the nurse call master device 7 and the like, a restoration button 447 for stopping a notification operation, and a corridor light second communication IF 448 for communicating with the plate slave device 2.

FIG. 6 is a functional block diagram illustrating the nurse call master device 7. As shown in FIG. 6, the nurse call master device 7 includes the handset 61, the loudspeaker 62, the master device sound processing unit 63, the master device monitor 64, the master device video processing unit 65, the operation unit 66, the master device CPU 67, the master device communication IF 68, and the information storage unit 69. The handset 61 operates for answering a call from the nurse call slave device 1. The loudspeaker 62 makes notification of a calling sound, an alarm sound, and the like. The master device sound processing unit 63 processes a sound signal and processes an alarm sound. The master device monitor 64 is implemented by an LCD for displaying various information. The master device video processing unit 65 processes a video image to be displayed on the master device monitor 64. The operation unit 66 is implemented by a touch panel for performing various operations. The master device CPU 67 controls the entire nurse call master device 7. The master device communication IF 68 communicates with another device such as the controller 8. The information storage unit 69 stores various information.

Figure 24:
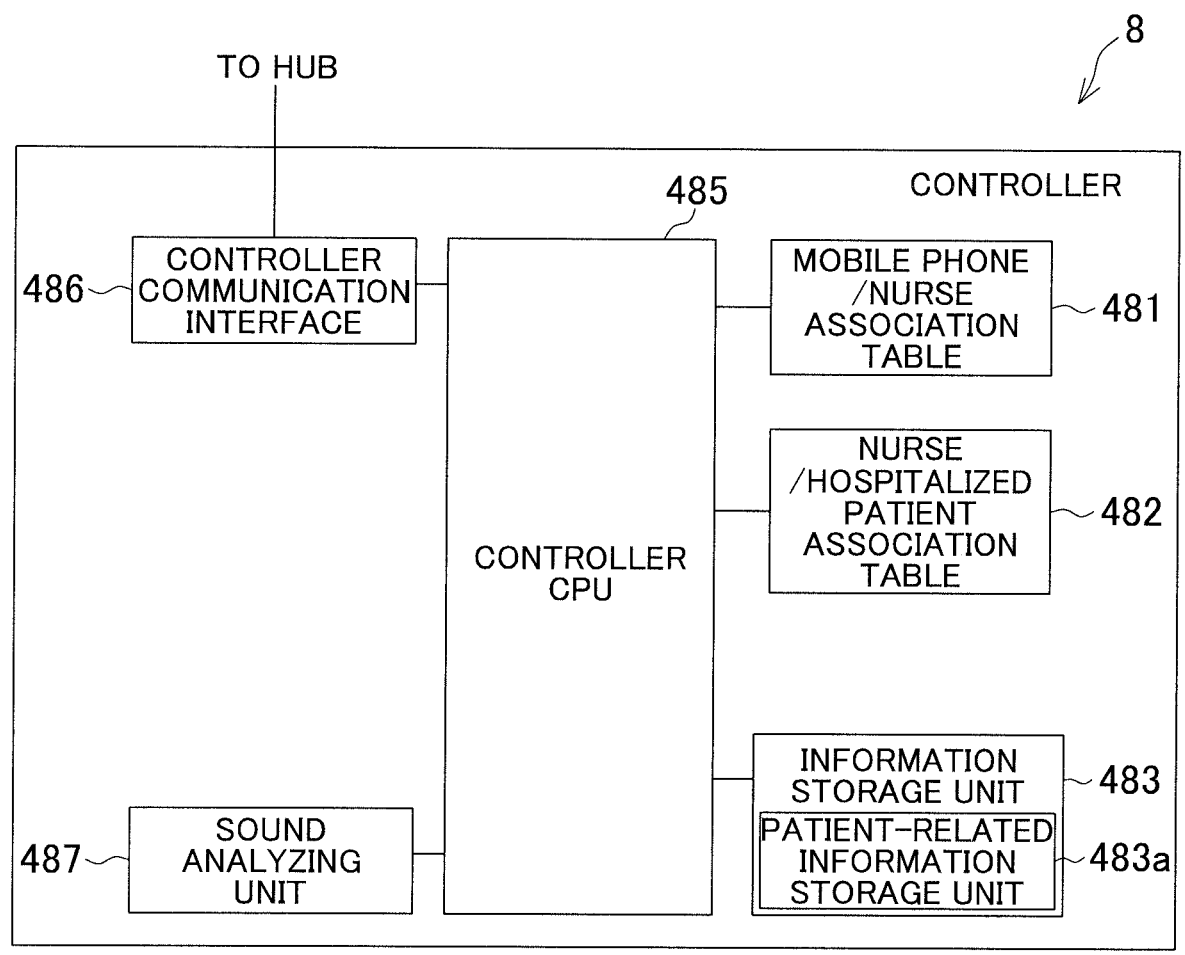
FIG. 24 is a functional block diagram illustrating a configuration of the controller 8 of the nurse call system according to the fifth embodiment.

FIG. 24 is a functional block diagram illustrating the controller 8. As shown in FIG. 24, the controller 8 includes a mobile phone/nurse association table 481 in which a nurse and the nurse mobile phone 9 are associated with each other, and a nurse/hospitalized patient association table 482 in which a nurse and a hospitalized patient are associated with each other. The controller 8 further includes an information storage unit 483 for storing various information, a controller CPU 485 for controlling the controller 8, a controller communication IF 486 for communicating with another device such as the nurse call master device 7, and a sound analyzing unit 487 for analyzing a sound inputted from the bedside monitor 3 or the like.

The information storage unit 483 includes a patient-related information storage unit 483a for storing patient-related information. The patient-related information storage unit 483a stores, for example, a relationship between patient information, and an ID of the bedside monitor 3 and an ID of the nurse call slave device 1. Such information is updated through operation on the nurse call master device 7.

Figure 25:
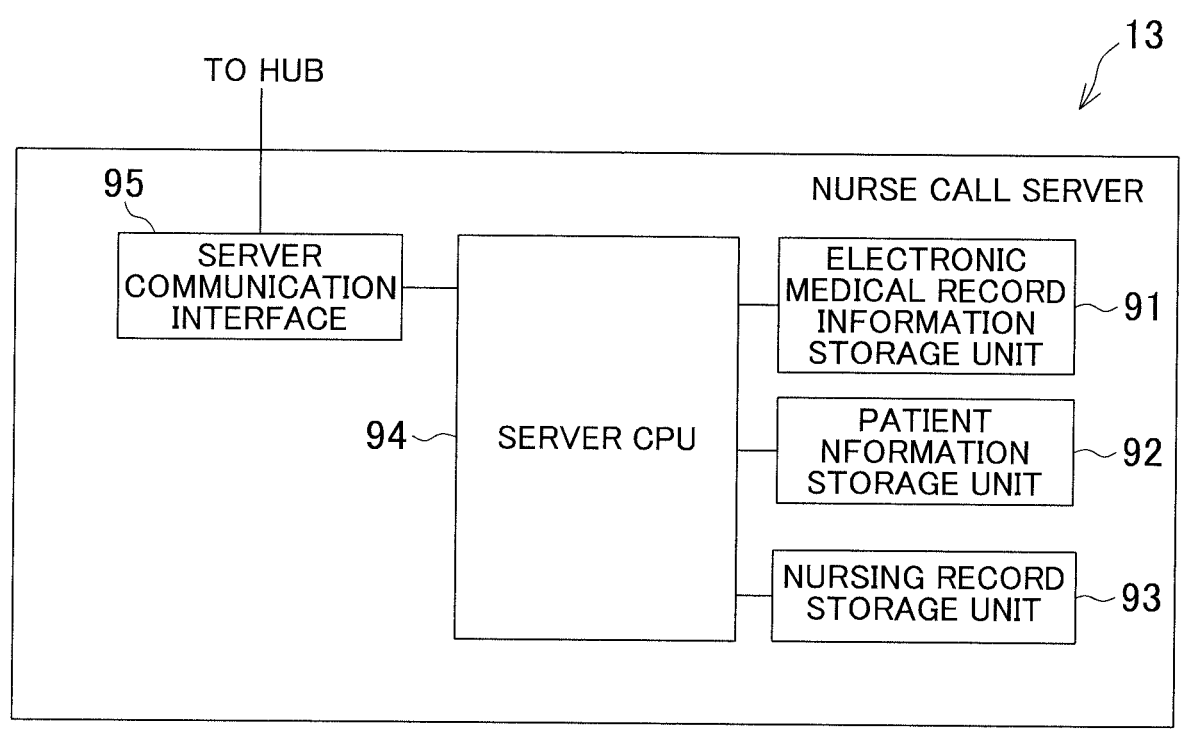
FIG. 25 is a functional block diagram illustrating a configuration of a nurse call server 13 of the nurse call system according to the fifth embodiment.

FIG. 25 is a functional block diagram illustrating the nurse call server 13. As shown in FIG. 25, the nurse call server 13 includes an electronic medical chart information storage unit 91 for storing a medical chart, of a patient, which is inputted by a doctor, a patient information storage unit 92 for storing various patient information, a nursing record storage unit 93 for storing nursing records inputted by a nurse, a server CPU 94 for controlling the nurse call server 13, and a server communication IF 95 for communicating with another device such as the controller 8.

The operation of the nurse call system having such a configuration will be described below. Calling for a nurse through an operation on the nurse call slave device 1, sound notification operations of the nurse call master device 7 and the nurse mobile phone 9 which are called, an answering operation through the operation on the nurse call master device 7, and an answering operation of the nurse mobile phone 9 are the same as in conventional art. Therefore, the description of such operations is omitted, and input of nursing records by a nurse and an operation performed according to the input will be described below.

Nursing records can be inputted by using the nurse call master device 7 or the bedside monitor 3 provided in the hospital room. Input from the nurse call master device 7 is the same as in conventional art and the description thereof is omitted. The flow of input from the bedside monitor 3 will be described below.

Firstly, the bedside monitor 3 is shifted to be in a sound input mode through a predetermined operation on the bedside monitor 3. When the mode has shifted to the sound input mode, a sound input mode shift signal is transmitted from the bedside monitor 3 to the controller 8, the sound analyzing unit 487 of the controller 8 is enabled, all the sounds inputted from the bedside monitor 3 are transmitted to the controller 8, and the sounds are analyzed.

In this state, a predetermined registered word is inputted as a sound. For example, in a case where the word "nursing records" is registered as the input start word for the nursing records, a nurse inputs the word as a sound through the microphone 34 of the bedside monitor 3, so that the sound analyzing unit 487 recognizes this sound and the mode shifts to a nursing records input mode. Then, the controller CPU 485 performs control to start communication between the nurse call server 13 and the controller 8, thereby allowing the nursing records to be inputted as a sound to the nurse call server 13.

The nurse can recognize that the mode has shifted to the nursing records input mode, through the display on the bedside monitor 3, and starts inputting a sound in response to the shift. In the nursing records input mode, in a case where the sound emitted toward the bedside monitor 3 includes, for example, words of "blood pressure xx, pulse yy", the sound analyzing unit 487 recognizes the words, and the "blood pressure xx, pulse yy" is recorded in the nursing record storage unit 93 of the nurse call server 13 and stored as the nursing records.

At this time, the controller 8 performs control to specify a patient associated with the bedside monitor 3 from the ID information of the bedside monitor 3 which is transmitted from the bedside monitor 3, based on the information stored in the patient-related information storage unit 483a, and also transmit the specified patient information to the nurse call server 13 and stored.

When the input has ended, the inputted nursing records can be confirmed through a predetermined operation. This confirmation can be performed through not only the bedside monitor 3 to which the nursing records have been inputted, but also another device such as the nurse mobile phone 9.

Thus, according to the fifth embodiment, the nursing records can be inputted from a hospital room of a patient for whom the treatment has been performed. Furthermore, the input can be made as a sound, thereby substantially reducing load of nursing work for inputting the nursing records.

The bedside monitor 3 is disposed near a hand, and input can be more easily performed to the bedside monitor 3 as compared with, for example, the plate slave device 2 disposed on the wall surface. The bedside monitor 3 is associated with the nurse call slave device 1 (bed) unlike the nurse mobile phone 9. Therefore, a patient for whom the input is performed can be recognized from the bedside monitor ID, and information for recognizing a patient for whom the nursing records are inputted need not be inputted together, and input can be performed through a simple operation.

Furthermore, the sound analyzing unit 487 is provided in the controller 8, and need not be provided for each bed or for each hospital room, thereby reducing increase of cost for the bedside monitor 3 or the plate slave device 2. In addition, the inputted nursing records can be confirmed at the location where the input has been performed, and the nurse who has performed the input operation can feel reassured.

In the above-described embodiment, the nursing records can be inputted as a sound through the bedside monitor 3. However, the nursing records may be inputted through another device, and may be inputted as a sound through the nurse mobile phone 9. Moreover, the nursing records may be inputted as a sound through the plate slave device 2 that includes the microphone 22, or may be inputted through the nurse call slave device 1 that includes a sound input unit.

The sound analyzing unit 487 is provided in the controller 8. However, the sound analyzing unit 487 may be provided in at least one of the controller 8, the nurse call server 13, and a cloud service (not shown). Alternatively, the sound analyzing unit 487 may be provided in a device that allows sound input.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

What is claimed is:

1. A nurse call system comprising:
a nurse call slave device provided for each bed in a hospital room for allowing a hospitalized patient to call a nurse;
a nurse call master device provided at a nurse station for answering a call from the nurse call slave device;
a plate slave device to which the nurse call slave device is connected, the plate slave device provided near a bed in the hospital room;
a bedside monitor provided for each bed in the hospital room, the bedside monitor capable of displaying patient-related information;
a corridor light provided in front of the hospital room for indicating a call from the nurse call slave device;
a control unit configured to control calling and speaking, and communication between devices; and
a plurality of nurse mobile phones to be carried by nurses for answering a call from the nurse call slave device,
wherein the plate slave device, the corridor light, or the control unit has an automatic answering unit for automatically answering a call from the nurse call slave device, and causes the automatic answering unit to automatically answer at least a part of calls from the nurse call slave device without calling the nurse call master device and the nurse mobile phones,
wherein the automatic answering unit includes a sound recognition unit,
wherein the automatic answering unit includes a keyword storage unit for storing a first keyword group including a plurality of keywords indicating a wrong call,
wherein, in a case where, when a call from the nurse call slave device has been automatically answered, a content in the call includes the first keyword group, a hospitalized patient who has made the call through the nurse call slave device is allowed to confirm whether or not the call from the nurse call slave device is to be cancelled, by using a sound or character information, through at least one device among the nurse call slave device, the plate slave device, and the bedside monitor of the hospitalized patient, and
wherein the call from the nurse call slave device is controlled to be cancelled when the hospitalized patient makes, through the device, a response indicating that the call from the nurse call slave device is to be cancelled, by using the sound or character information.

2. The nurse call system according to claim 1, wherein the plate slave device, the corridor light, or the control unit performs control to call the nurse call master device or the nurse mobile phones without answering performed automatically by the automatic answering unit when a predetermined urgent call occurs.

3. The nurse call system according to claim 1, comprising a nurse mobile phone table storage unit in which a nurse and each nurse mobile phone are associated with each other, and an assigned nurse table storage unit in which a nurse and a hospitalized patient are associated with each other,
wherein the keyword storage unit further stores a second keyword group indicating that handling by an assigned nurse is required, and
wherein, in a case where, when a call from the nurse call slave device has been automatically answered, a content in the call includes the second keyword group, the automatic answering unit is controlled to call the nurse mobile phone of a nurse associated with a hospitalized patient that has made the call from the nurse call slave device.

4. The nurse call system according to claim 3, wherein the keyword storage unit further stores a third keyword group indicating that highly urgent handling is not required, and
wherein, in a case where, when a call from the nurse call slave device has been automatically answered, a content in the call includes the third keyword group, the automatic answering unit is controlled to transmit a message indicating the content in the call from a hospitalized patient who has made the call from the nurse call slave device, to the nurse mobile phone of a nurse associated with the hospitalized patient.

5. The nurse call system according to claim 1, wherein a location information transmitter for wirelessly transmitting a location signal is disposed at an appropriate place in a hospital ward, and a location management server for storing location information of each of the nurse mobile phones is provided,
wherein each nurse mobile phone includes a location information communication unit for receiving the location signal transmitted by the location information transmitter, and transmitting the location signal with an ID of the nurse mobile phone added thereto,
wherein the location management server includes a nurse mobile phone location storage unit for storing the location information received from each nurse mobile phone, a bed location storage unit for storing a location of the individual nurse call slave device, and a distance measurement unit for measuring a distance between each nurse mobile phone and the nurse call slave device that has made a call, and selecting a nurse mobile phone that satisfies a predetermined condition including the distance,
wherein the keyword storage unit further stores a fourth keyword group indicating that handling by a nurse is required, and
wherein in a case where, when a call from the nurse call slave device has been automatically answered, a content in the call includes the fourth keyword group, the automatic answering unit is controlled to cause the distance measurement unit to select a nurse mobile phone near the nurse call slave device, and call the selected nurse mobile phone.

6. The nurse call system according to claim 4, wherein the location information transmitter for wirelessly transmitting the location signal is disposed at an appropriate place in a hospital ward, and the location management server for storing location information of each of the nurse mobile phones is provided,
wherein each nurse mobile phone includes the location information communication unit for receiving the location signal transmitted by the location information transmitter, and transmitting the location signal with an ID of the nurse mobile phone added thereto,
wherein the location management server includes the nurse mobile phone location storage unit for storing the location information received from each nurse mobile phone, the bed location storage unit for storing a location of the individual nurse call slave device, and the distance measurement unit for measuring a distance between each nurse mobile phone and the nurse call slave device that has made a call, and selecting the nurse mobile phone that satisfies the predetermined condition including the distance, and
wherein, in a case where, when a call from the nurse call slave device has been automatically answered, a content in the call does not include any of the first keyword group to the third keyword group, the automatic answering unit is controlled to cause the distance measurement unit to select the nurse mobile phone near the nurse call slave device, and call the selected nurse mobile phone.

* * * * *